United States Patent
De Groof et al.

(10) Patent No.: US 12,297,459 B2
(45) Date of Patent: May 13, 2025

(54) PORCINE ROTAVIRUS

(71) Applicant: Intervet Inc., Madison, NJ (US)

(72) Inventors: Ad De Groof, Groesbeek (NL); Paul Vermeij, St. Anthonis (NL); Cornelia Maria Van der Hoek, Amsterdam (NL); Martin Deijs, Huizen (NL)

(73) Assignee: Intervet Inc., Rahway, NJ (US)

( * ) Notice: Subject to any disclaimer, the term of this patent is extended or adjusted under 35 U.S.C. 154(b) by 684 days.

(21) Appl. No.: 17/291,769

(22) PCT Filed: Nov. 11, 2019

(86) PCT No.: PCT/EP2019/080811
§ 371 (c)(1),
(2) Date: May 6, 2021

(87) PCT Pub. No.: WO2020/099293
PCT Pub. Date: May 22, 2020

(65) Prior Publication Data
US 2022/0220452 A1  Jul. 14, 2022

(30) Foreign Application Priority Data
Nov. 12, 2018 (EP) .................................. 18205672

(51) Int. Cl.
C07K 14/005 (2006.01)
C07K 14/14 (2006.01)
C07K 16/10 (2006.01)
C12N 7/00 (2006.01)
C12N 15/46 (2006.01)

(52) U.S. Cl.
CPC .............. C12N 7/00 (2013.01); C07K 14/005 (2013.01); *C12N 2720/12321* (2013.01); *C12N 2720/12322* (2013.01); *C12N 2720/12334* (2013.01)

(58) Field of Classification Search
CPC ........ C07K 14/005; C12N 2720/12321; C12N 2720/12322; C12N 2720/12334; C12N 7/00
See application file for complete search history.

(56) References Cited

FOREIGN PATENT DOCUMENTS

| | | |
|---|---|---|
| CN | 106459928 A | 2/2017 |
| CN | 107875379 A | 4/2018 |
| EP | 0235391 B1 | 6/1992 |
| JP | S63115825 A | 5/1988 |
| RU | 2443430 C2 | 2/2012 |
| WO | WO 2015158798 A1 | 10/2015 |
| WO | WO 2006099561 A1 | 9/2017 |

OTHER PUBLICATIONS

Genbank KX869732.1, submitted Jul. 2017:pdf 1.*
Alekseev, et al, Genome Characterization of a Pathogenic Porcine Rotavirus B Strain Identified in Buryat Republic, Russia in 2015, Pathogens, 2018, pp. 46, vol. 7.
Kazufumi Kugo et al, Genetic diversity and classification of the outer capsid glycoprotein VP7 of porcine group B rotaviruses, Arch Virol, 2009, pp. 1785-1795, vol. 154, Springer.
Marthaler et al, Detection of substantial porcine group B rotavirus genetic diversity in the United States, resulting in a modified classification proposal for G genotypes, Virology, 2012, pp. 85-96, vol. 433, Elsevier.
Marthaler et al, Rapid detection and high occurrence of porcine rotavirus A, B, and C by RT-qPCR in diagnostic samples, ournal ofVirological Methods, 2014, pp. 30-34, vol. 209, Elsevier.
Entry date: 2017. XP002787684 retrieved from EBI accession No. Uniprot: ADA221SDV7.
XP002787683 retrieved from EBI accession No. UNIPROT: DOFYJ7, entry date: 2009.
XP002787471 retrived from EBI accession No. EMBL: AB490426, entry date: 2009.
XP002787472 retrieved from EBI accession No. EMBL: KX869732, entry date: 2017.
Briko, 2001, "Criteria for assessing the effectiveness of vaccination," Medical scientific and practical portal, #03/01 [online], Apr. 2, 2001, [retrieved on Jun. 12, 2024]. Retrieved from the Internet:<URL: https://www.lvrach.ru/2001/03/4528644>. In Russian with machine English translat on (16 pages).
Kuga et al., 2009, "Genetic diversity and classification of the outer capsid glycoprotein VP7 of porcine group B rotaviruses," Arch. Virol., 154(11):1785-1795.
Yang et al., 2016 "Isolation and identification of one strain of porcine rotavirus," Animal Husbandry & Veterinary Medicine, 48(9):32-37 (in Chinese with English abstract).

* cited by examiner

*Primary Examiner* — Barry A Chestnut
(74) *Attorney, Agent, or Firm* — Susann Benn

(57) ABSTRACT

The present invention pertains to a novel rotavirus, especially an isolated virus, which is a member of the subspecies of porcine group B rotavirus (porcine RVB), causing diarrheal disease in pigs, to DNA fragments and corresponding proteins of the said virus, to vaccines on the basis of said virus, DNA and/or protein and to antibodies reactive with said virus and/or protein and diagnostic test kits for the detection of said virus.

19 Claims, No Drawings
Specification includes a Sequence Listing.

PORCINE ROTAVIRUS

CROSS-REFERENCE TO RELATED APPLICATIONS

This application is a National Stage application of International Patent Application No. PCT/EP2019/080811, filed Nov. 11, 2019, which claims priority to patent application Ser. No. 18/205,672.1, filed Nov. 12, 2018.

REFERENCE TO SEQUENCE LISTING SUBMITTED ELECTRONICALLY

The sequence listing of the present application is submitted electronically via EFS-Web as an ASCII formatted sequence listing with a file name "24609-US-PCT SL.txt", with a creation date of Sep. 23, 2021, and a size of 73,272 bytes. This sequence listing submitted via EFS-Web is part of the specification and is herein incorporated by reference in its entirety.

The present invention pertains to a novel rotavirus causing diarrheal disease in pigs, to nucleic acid fragments and corresponding proteins of the said virus, to vaccines on the basis of said virus, nucleic acid and/or protein and to antibodies reactive with said virus and/or protein and diagnostic test kits for the detection of said virus.

GENERAL BACKGROUND

Over the last decades, world-wide a strong increase is seen in the consumption of pig meat. As a consequence, an increase is seen in the number and the size of farms, in order to meet the increasing needs of the market. As is known from animal husbandry in general, large numbers of animals living closely together are vulnerable to all kinds of diseases. Moreover, farming of large numbers of animals increases the danger of infection with such diseases. One of these diseases that especially occur in young animals, such as pigs, is an infection with rotavirus.

Rotavirus (RV) is well established as a major cause of acute gastroenteritis in young children and animals, including nursing and weaned piglets. Rotaviral enteritis is a mild to severe disease characterized by nausea, vomiting, watery diarrhea and low-grade fever. Once a subject is infected by the virus, there is an incubation period of about two days before symptoms appear. The period of illness is acute. Symptoms often start with vomiting followed by four to eight days of profuse diarrhea. Dehydration is more common in rotavirus infection than in most of those caused by bacterial pathogens, and is the most common cause of death related to rotavirus infection. Further, these rotaviruses are a potential reservoir for genetic exchange with human rotaviruses. As a pathogen of livestock, notably in young calves and piglets, rotaviruses cause economic loss to farmers because of costs of treatment associated with high morbidity and mortality rates.

RVs belong to the Reoviridae family, possess a genome composed of 11 segments of double-stranded RNA (dsRNA) and are currently classified into eight groups (A-H) based on antigenic properties and sequence-based classification of the inner viral capsid protein 6 (VP6). While human RVA and RVC have been described around the world, current reports indicate that human RVB strains have been described only in China. Porcine RVB were first identified in the 1980s.

Serological and molecular characterization of RVB strains is limited due to the difficulty of adapting RVB strains to cell culture. Classification of porcine RVB strains based on pairwise identities of the genes encoding the outer capsid protein VP7 has been proposed by Kuga et al., 2009 (Arch Virol. 2009; 154(11):1785-95) and Marthaler et al., 2012 (Virology. 2012 Nov. 10; 433(1):85-96). Kuga et al. sequenced the VP7 of 38 porcine RVB strains and constructed phylogenetic trees and pairwise identity frequency graphs for G genotype classification purposes. Based on their analyses, they proposed 5 genotypes which were further divided into 12 clusters, using 67% and 76% nucleotide cut-off values. Marthaler et al. developed an adapted VP7 classification (in the following the "Marthaler classification") using previously published and newly sequenced RVB strains, resulting in 20 G genotypes based on an 80% nucleotide identity cut off value.

Rotavirus outer capsid proteins VP7 and VP4 have been well established to be capable of inducing independent neutralizing antibodies (Greenberg et al., J. Virol., 1983, 47:267-275; Hoshino et al., Proc. Natl. Acad. Sci. USA, 1985, 82:8701-8704) and associated protection against disease. While VP4 is located on the surface of the virion that protrudes as a spike, VP7 is a glycoprotein that forms the outer surface of the virion. Apart from its structural functions, it determines the G-genotype of the strain and, along with VP4, is involved in immunity to infection.

Recently, a neonatal diarrhea outbreak was observed in piglets in a farm in Spain, although the sows were vaccinated against RVA. Thus, maternal antibodies against RVA should have been present in the colostrum due to vaccination. Thus, samples were collected from infected subjects and analyzed for the presence of viruses.

A nucleic acid sequence belonging to a rotavirus B VP7 protein was found, which can be linked to the presence of RVB in the samples. The presence of RVB in the samples could also explain the clinical observations. The almost full-length nucleotide sequence encoding the VP7 protein is presented in SEQ ID NO: 1.

It was surprisingly found by genetic analyses that the VP7 sequence detected in the samples was genetically distinct from VP7 sequences from known RVB genotypes. Thus, it was concluded that the subjects suffered from a previously unknown disease causing RVB type.

OBJECT OF THE INVENTION

It is thus an objective of the present invention to provide a new infectious agent associated with diarrhea in pigs as well as vaccines aiming at protecting, i.e. preventing, ameliorating and/or treating, a pig against the disease or at least reducing symptoms of the disease and/or decreasing the mortality of the disease. Moreover, it is an objective of the present invention to provide means to detect and identify the disease-associated infectious agent.

SUMMARY OF THE INVENTION

The present invention provides an isolated rotavirus which is a member of the sub-species of porcine group B rotaviruses genotype G12, which in its wild type form causes (neonatal) diarrhea in pigs, said virus being characterized in that it has a viral genome comprising an open reading frame having a nucleotide sequence corresponding to the nucleotide sequence depicted in SEQ ID NO: 1 or a nucleotide sequence having a level of identity of at least 90% therewith. Although the present virus is in fact an RNA virus, it is common to express that an open reading frame of the viral genome has a level of identity corresponding to a particular DNA sequence. As is commonly known, this expresses that the actual RNA sequence of the viral genome can be transcribed from that DNA sequence.

Further, the present invention provides a nucleic acid fragment (either DNA or RNA) comprising an open reading frame comprising at least 100 nucleotides, characterized in that said nucleic acid fragment has a level of identity of at least 90% to the nucleotide sequence depicted in SEQ ID NO: 1, as well as a protein encoded by the nucleic acid fragment. Preferably the fragment comprises more than 100 nucleotides, such as 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 730 up to 740 nucleotides.

The present invention further provides an outer viral capsid glycoprotein VP7, characterized that it is encoded by a nucleic acid fragment having a level of identity of at least 90% to the nucleotide sequence depicted in SEQ ID NO: 1. An example of such a protein is depicted in SEQ ID NO: 2.

The present invention further provides a vaccine for protecting a pig against an infection caused by porcine RVB, characterized in that said vaccine comprises an immunogenically effective amount of a virus as described herein and a pharmaceutically acceptable carrier.

The present invention further provides a vaccine for protecting a pig against an infection caused by porcine RVB, characterized in that said vaccine comprises an immunologically effective amount of a protein or an outer viral capsid glycoprotein VP7 or a nucleic acid fragment as described herein, and a pharmaceutically acceptable carrier.

The vaccine may be used in prophylactically treating an animal.

The present invention further provides an antibody or antiserum reactive with a virus or with a protein or with an outer viral capsid glycoprotein VP7 as described herein.

The present invention further provides a diagnostic test kit for the detection of antibodies reactive with a virus or with antigenic material thereof or reactive with a protein or reactive with an outer viral capsid glycoprotein VP7 as described herein.

The present invention further provides a diagnostic test kit for the detection of a virus or antigenic material thereof or an outer viral capsid glycoprotein VP7 as described herein.

DETAILED DESCRIPTION OF THE INVENTION

It has been found that the causative agent of the disease symptoms described above may be linked to the presence of a novel rotavirus B (RVB), in particular a disease causing RVB of the G12 genotype. Although RVB of genotype G12 has been isolated from diseased pigs infected with various rotaviruses (see Marthaler 2012), this is the first time a RVB of genotype 12 is unambiguously associated with disease in pigs. Genetic analyses revealed that the nucleotide sequence found in the samples belong to an open reading frame of an outer viral capsid protein VP7 (in short: "VP7 capsid protein" or "VP7") of RVB. The nucleotide sequence of the DNA fragment is depicted in SEQ ID NO: 1. The corresponding amino acid sequence is depicted in SEQ ID NO: 2.

The maximum identity of the almost full-length DNA fragment of SEQ ID NO: 1 with known DNA sequences is 87% identity with a porcine VP7 gene classified as genotype G12 included in the classification proposal by Marthaler et al., 2012. The VP7 classification proposed by Marthaler et al. resulted in 20 G genotypes based on an 80% nucleotide identity cut off value. However, Marthaler et al. also reported an overlap between inter- and intra-genotype identities. Next to this, none of the G12 genotype RotaB viruses has ever been unambiguously associated with disease in pigs, let alone with neonatal diarrhea.

For this reason, the inventors decided to tentatively place the nucleotide sequence of SEQ ID NO: 1 as belonging to a novel virus, especially a novel porcine RVB, in particular an RVB of a novel genotype, the virus containing a VP7 encoding gene with highest similarities to the G12 genotype within the Marthaler classification.

A phylogenetic tree showing the relation between the VP7 DNA sequence of the novel virus according to the invention with known VP7 sequences of RVB is provided in FIG. 1, consisting of two subfigures, the first one denoted as "Figure B", the second one denoted as "Figure A". The phylogenetic tree was created with MEGA-X software using the neighbor-joining method, with pairwise deletion in case of gaps or insertions. Reference: Tamura K, et al., MEGA6: molecular evolutionary genetics analysis using maximum likelihood, evolutionary distance, and maximum parsimony methods. Mol. Biol. Evol. 2011; 28: 2731-2739. The new virus is referred to in this tree (first part, lower section) as New RotaB VP7 Spain.

Thus, in one embodiment the present invention provides the VP7 protein encoded by the DNA fragment of SEQ ID NO: 1 for use as an antigen in a method for protecting pigs against a pathogenic infection with porcine RVB, and in particular against a pathogenic infection with porcine RVB of the G12 genotype. The VP7 protein is typically comprised in a vaccine composition, i.e. a composition safe to be administered to pigs, and in which VP7 is mixed with a pharmaceutically acceptable carrier, as will be described below.

It will be understood that for these genes and proteins natural variations can exist between individual representatives of rotavirus. Genetic variations leading to minor changes in e.g. the capsid protein sequences, such as VP7, do exist. First of all, there is the so-called "wobble in the second and third base" explaining that nucleotide changes may occur that remain unnoticed in the amino acid sequence they encode: e.g. triplets TTA, TTG, TCA, TCT, TCG and TCC all encode Leucine. In addition, minor variations between representatives of the novel virus according to the invention may be seen in amino acid sequence. These variations can be reflected by (an) amino acid difference(s) in the overall sequence or by deletions, substitutions, insertions, inversions or additions of (an) amino acid(s) in said sequence Amino acid substitutions which do not essentially alter biological and immunological activities, have been described, e.g. by Neurath et al. in "The Proteins" Academic Press New York (1979) Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science 227, 1435-1441, 1985) and determining the functional similarity between homologous proteins. Such amino acid substitutions of the exemplary embodiments of this invention, as well as variations having deletions and/or insertions are within the scope of the invention.

This explains why the VP7 protein, when isolated from different representatives of a porcine rotavirus according to the invention, may have homology levels that are significantly below 100%, while still representing the VP7 protein of the porcine rotavirus according to the invention.

This is clearly reflected e.g. in the phylogenetic tree in FIG. 3 of the paper by Marthaler et al., 2009 cited above, where it is shown that even within one single clade the VP7 encoding nucleotide sequences nevertheless have significantly different overall genomic nucleotide sequences.

Thus, the virus according to the invention is described i.a. as an isolated virus being characterized in that it its genome comprises a nucleotide sequence that corresponds to a nucleotide sequence having a level of identity of at least 90% to the nucleotide sequence depicted in SEQ ID NO: 1. In particular, the virus according to the invention is characterized in that it is a rotavirus, which is a member of the sub-species of porcine group B rotavirus (porcine RVB), and wherein the nucleotide sequence depicted in SEQ ID NO: 1 belongs to an open reading frame encoding a VP7.

For the purpose of this invention, a "level of identity" is to be understood as the level of identity of the sequence of SEQ ID NO: 1 and/or the corresponding region encoding the VP7 of a porcine rotavirus and/or the corresponding amino acid sequence of which the level of identity has to be determined. A suitable program for the determination of a level of identity is the nucleotide blast program (blastn) of NCBFs Basic Local Alignment Search Tool, using the "Align two or more sequences" option and standard settings (http://blast.ncbi.nlm.nih.gov/Blast.cgi). Therein, the identities are based on the (standard) Blastn algorithm that is used in BLAST (Stephen Altschul, Warren Gish, Webb Miller, Eugene Myers, and David J. Lipmann at National Institutes of Health (NIH), Journal of Molecular Biology, 1990).

The virus according to the invention is typically an isolated virus. For the purpose of this invention, "isolated" means: set free from tissue with which the virus is associated in nature.

A preferred form of this embodiment relates to a virus, such as an isolated virus, that comprises a nucleotide sequence that has a level of identity of at least 91%, more preferably at least 92%, 93%, 94%, 95%, 96%, 97%, 98%, 99% or even 100%, in that order of preference, to the nucleotide sequence as depicted in SEQ ID NO: 1.

The virus according to the invention can be in a live, a live attenuated or an inactivated form. As indicated above, the DNA sequence of the gene encoding the VP7 of the virus is characterized. The identification of the nucleotide sequence of SEQ ID NO: 1 as belonging to an ORF encoding a VP7 is highly useful, since it can now be used i.a. as a basis for DNA or RNA vaccines, for use in the preparation of subunit vaccines on the basis of the encoded protein, or for diagnostic purposes, as will extensively be explained below.

Therefore, in another embodiment, the present invention relates to a nucleic acid fragment (e.g. DNA or RNA) comprising an open reading frame comprising at least 100, preferably at least 200, more preferably at least 300, 400 or 500 nucleotides, characterized in that said nucleic fragment has a level of identity of at least 90% to the nucleotide sequence depicted in SEQ ID NO: 1, preferably at least 91%, more preferably at least 92%, 93%, 94%, 95%, 96%, 97%, 98%, 99% or even 100%, in that order of preference, to the nucleotide sequence depicted in SEQ ID NO: 1.

In still another embodiment, the present invention relates to a nucleic acid fragment as described above, characterized in that the open reading frame encodes a VP7 or a fragment thereof.

The term "fragment thereof" as used in the present invention may relate to any smaller part of the full-length VP7 protein. For use in vaccination, such parts should be suitable to impart immunogenic properties, i.e. the fragment is functional in inducing an immune response in the vaccinated subject, and this can be designated as "immunogenic fragment".

The nucleic acid fragment according to the present invention may be brought into a form suitable for heterologous expression of the encoded protein. Such a form may be a vector or other form suitable for heterologous expression of viral nucleic acid. Typically, the vector contains a promotor suitable for heterologous expression. Thus, in a preferred embodiment, the nucleic acid fragment according to the present invention is under the control of a heterologous promoter or is introduced into an open reading frame under the control of a heterologous promoter.

Therefore, in another embodiment, the present invention relates to a protein, in particular an outer viral capsid glycoprotein VP7 encoded by the nucleic acid fragment according to the present invention, or a fragment thereof, produced in a heterologous expression system. A preferred form of this embodiment relates to a VP7 having the amino acid sequence as depicted in SEQ ID NO: 2.

Such VP7 of the virus according to the invention are suitable for use as an antigen, in particular for use as an antigen in vaccines, more specifically in subunit vaccines. Further, they can be used to raise antibodies. Furthermore, they make diagnostic tests possible, as explained below.

Further, the present invention provides the nucleotide and amino acid sequences of the entire coding regions of the different proteins of the novel virus, confirming that the novel virus belongs to a rotavirus. The nucleotide and amino acid sequences provided by the present invention are given by the SEQ ID NO. 1-22 as follows:

| Segment, Nr | Type | Protein | Sequence, Nr. |
|---|---|---|---|
| 1 | Nucleotide | | SEQ ID NO: 3 |
| 1 | Amino acid | VP1 Pol | SEQ ID NO: 4 |
| 2 | Nucleotide | | SEQ ID NO: 5 |
| 2 | Amino acid | VP2 | SEQ ID NO: 6 |
| 3 | Nucleotide | | SEQ ID NO: 7 |
| 3 | Amino acid | VP3 | SEQ ID NO: 8 |
| 4 | Nucleotide | | SEQ ID NO: 9 |
| 4 | Amino acid | VP4 (VP8*, VP5*) | SEQ ID NO: 10 |
| 5 | Nucleotide | | SEQ ID NO: 11 |
| 5 | Amino acid | NSp1 | SEQ ID NO: 12 |
| 6 | Nucleotide | | SEQ ID NO: 13 |
| 6 | Amino acid | VP6 | SEQ ID NO: 14 |
| 7 | Nucleotide | | SEQ ID NO: 15 |
| 7 | Amino acid | NSp3 | SEQ ID NO: 16 |
| 8 | Nucleotide | | SEQ ID NO: 17 |
| 8 | Amino acid | NSp2 | SEQ ID NO: 18 |
| 9 | Nucleotide | | SEQ ID NO: 1 |
| 9 | Amino acid | VP7 | SEQ ID NO: 2 |
| 10 | Nucleotide | | SEQ ID NO: 19 |
| 10 | Amino acid | NSp4 | SEQ ID NO: 20 |
| 11 | Nucleotide | | SEQ ID NO: 21 |
| 11 | Amino acid | NSp5 | SEQ ID NO: 22 |

*VP4 is an open reading frame that encodes a preprotein that is subsequently cleaved into VP5 and VP8

Thus, the virus according to the invention may further be described as an isolated virus being characterized in that it its genome comprises a nucleotide sequences that correspond to a nucleotide sequences each having a level of identity of at least 90% to the nucleotide sequences depicted above encoding the proteins of Segments 1-11, i.e. to the nucleotide sequences of SEQ ID NO: 1, 3, 5, 7, 9, 11, 13, 15, 17, 19 and 21.

It is one of the merits of the present invention that it is now for the first time possible to analyze the presence or absence of the novel rotavirus in the various organs and body fluids of pigs suffering from viral diarrhea, or other signs and symptoms associated with rotavirus infection, and to treat the disease or prevent outbreak of the disease in healthy animals by administering to the animal a vaccine as described in the following.

A "vaccine" according to the present invention is a pharmaceutical composition that is safe to administer to a subject animal, and is able to induce protective immunity in that animal against a pathogenic micro-organism, i.e. to induce protection against the micro-organism.

"Protection" against a micro-organism means aiding in preventing, ameliorating and/or treating (including curing) a pathogenic infection with that micro-organism or a disorder arising from that infection, for example to prevent or reduce one or more clinical signs resulting from the infection with the pathogen.

Thus, another embodiment of the present invention relates to a vaccine for protecting, i.e. preventing, ameliorating and/or treating, against a rotavirus infection in pigs, in particular infections caused by porcine RVB, further particularly infections caused by porcine RVB of the G12 genotype, wherein such vaccines comprise a virus according to the invention and a pharmaceutically acceptable carrier. Protecting in this respect should thus be interpreted to comprise vaccination in order to prevent the outbreak of the disease, i.e. (neonatal) diarrhea or gastroenteritis caused by viral infection, as well as vaccination to diminish the symptoms of the disease.

Preferably, the vaccine according to the invention is used for preventing the disease given the short time between infection and outbreak of the disease of about two days and given that viral diarrhea is highly contagious.

In another embodiment, the present invention relates to a vaccine for protecting against neonatal diarrhea caused by infection with porcine RVB. Therefore, the present invention is further directed to a vaccine for sow vaccination.

"Sow vaccinations" in the present invention means prepartum immunization of sows to convey passive immunity to piglets and provide protection against an infection with the porcine RVB as described herein. By inducing antibodies in the female animal, piglets arrive at adequate protection against the infection through the intake of colostrum of the vaccinated animal. Therefore, an antigen that is shown to have a protective effect in piglets, can be useful for vaccinating sows to arrive at a clear protective effect in piglets, typically at least in the window between day 0 and day 21 after birth.

The present invention thus also pertains to the use of a vaccine as described herein for vaccination of a female pig and allowing the piglet to take up colostrum form the vaccinated female pig. To arrive at optimum protection, the colostrum is typically taken up within 48 hours, in particular within 24 hours after birth of the piglet.

Examples of pharmaceutically acceptable carriers that are suitable for use in a vaccine according to the invention are, for example, sterile water, saline, and aqueous buffers such as PBS. In addition, a vaccine according to the invention may comprise other additives such as adjuvants, stabilizers, anti-oxidants and others, as described below.

A vaccine according to the invention may comprise the virus according to the invention in attenuated live or inactivated form.

Attenuated live virus vaccines, i.e. vaccines comprising the virus according to the invention in a live attenuated form, have the advantage over inactivated vaccines that they best mimic the natural way of infection. In addition, their replicating abilities allow vaccination with low amounts of viruses; their number will automatically increase until it reaches the trigger level of the immune system. From that moment on, the immune system will be triggered and will finally eliminate the viruses. A live attenuated virus is a virus that has a decreased level of virulence when compared to virus isolated from the field. A virus having a decreased level of virulence is considered a virus that does not cause the typical symptoms of viral infection. A possible disadvantage of the use of live attenuated viruses however might be that inherently there is a certain level of virulence left. This is not a real disadvantage as long as the level of virulence is acceptable, i.e. as long as the vaccine at least prevents the pigs from suffering from diarrhea or other typical symptoms of the infection. Of course, the lower the rest virulence of the live attenuated vaccine is, the less influence the vaccination has on weight gain during/after vaccination. Therefore, one preferred form of this embodiment of the invention relates to a vaccine comprising a virus according to the invention wherein said virus is in a live attenuated form.

Attenuated viruses can e.g. be obtained by growing the viruses according to the invention in the presence of a mutagenic agent, followed by selection of virus that shows a decrease in progeny level and/or in replication speed. Many such agents are known in the art.

Inactivated vaccines are, in contrast to their live attenuated counterparts, inherently safe, because there is no rest virulence left. In spite of the fact that they usually comprise a somewhat higher dose of viruses compared to live attenuated vaccines, they may e.g. be the preferred form of vaccine in pigs that are suffering already from other diseases. Pigs that are kept under sub-optimal conditions, such as incomplete nutrition or sub-optimal housing would also benefit from inactivated vaccines.

Therefore, another preferred form of this embodiment relates to a vaccine comprising a virus according to the invention wherein said virus is in an inactivated form.

The standard way of inactivation is a classical treatment with formaldehyde. Other methods well-known in the art for inactivation are UV-radiation, gamma-radiation, treatment with binary ethylene-imine, and thimerosal. The skilled person knows how to apply these methods. Preferably the virus according to the invention is inactivated with β-propiolactone, glutaraldehyde, ethylene-imine or formaldehyde. It goes without saying that other ways of inactivating the virus are also embodied in the present invention.

Although whole inactivated rotavirus provides a good basis for vaccines, their production may be expensive and laborious. In particular, adapting porcine RVB strains to cell culture is still found difficult in the art (Sanekata et al., J Clin Microbiol. 1996 March; 34(3): 759-761).

An alternative approach is to develop subunit or recombinant vaccines by expressing one or more rotavirus proteins or immunogenic parts thereof which retain the neutralizing epitopes necessary for effective recognition by the host cell. Both VP7 and VP4, the two protein components of the outer capsid, react with neutralizing antibodies, and monoclonal antibodies (MAbs) directed at either of these proteins are capable of neutralizing rotavirus.

VP7 is the major outer capsid protein and is primarily responsible for determining the viral antigenic characteristics. It is a highly immunogenic glycoprotein and it is thus a primary candidate for inclusion in a subunit vaccine. Hence, an attractive alternative for the use of whole viruses is the use of rotavirus subunits, more preferably the use of the subunit formed by VP7. Subunits formed by VP7 have the advantage that they do not have to be inactivated before use in a vaccine, and therefore they have the additional advantage that they are intrinsically safe. Further, cloning and heterologous expression systems for the heterologous production of such subunits are available and established in the art, as described below. Further, it has been shown that recombinant VP7 mediates native antigenic determinants in the absence of other rotavirus proteins (Khodabandehloo et al., Iran J Public Health. 2012; 41(5): 73-84.).

Recombinant vaccines can also be provided as nucleic acid construct containing vaccines such as DNA and RNA vaccines, including synthetic messenger RNA, RNA replicons, and naked DNA vectors. One such vaccination strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)] which have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health 6 Res Rev.* 13(1):1-9. (2012)]. The RP platform has been used to encode pathogenic antigens and is the basis for several USDA-licensed vaccines for swine and poultry.

Thus, another embodiment of the present invention relates to vaccines for protecting, i.e. preventing, ameliorating or treating, a pig against a rotavirus infection, in particular infections caused by porcine RVB, further particularly infections caused by porcine RVB of the G12 genotype, wherein such vaccines comprise an immunogenically effective amount of the VP7 protein or immunogenic fragments thereof, or corresponding nucleic acid constructs, and a pharmaceutically acceptable carrier.

Expression of rotavirus VP7 has been reported in the art for *E. coli*, herpes virus, vaccinia virus in mammalian cells and baculovirus. However, most of them were not full-length VP7 protein. Advanced technique in anchoring the simian rotavirus SA11 VP7 to the surface of eukaryotic cells (VP7sc) has done using recombinant vaccinia virus and adenoviruses. The expressed VP7 protein appeared to be both antigenic and immunogenic and induced passive protection against rotavirus disease in mice (Both et al., Virology. 1993; 193:940-950).

Using the right system for viral gene expression is very important in producing biologically active recombinant protein. Baculovirus expression system has some unique features that made it the system of choice for many protein expressions, such as solubility, correctly folding, signal peptide cleavage, oligomerization, functional activity, phosphorylation, and glycosylation of recombinant proteins. Baculovirus has been used successfully in the art as an expression system for the production of rotavirus proteins (McGonigal T P et al., Virus Res. 1992; 23(1-2):135-150; Redmont M J et al., Vaccine. 1993; 11:273-281.; Fiore L et al., J Gen Virol. 1995; 76(Pt 8):1981-1988). The baculovirus system is thus a candidate for the expression of VP7 in that it offers the possibility of synthesis of a recombinant protein in high yield with the conformational requirements necessary to permit immunological and functional studies (Fiore L et al., J Gen Virol. 1995; 76(Pt 8):1981-1988; Ishida S I et al. J clin Microbiol. 1996; 34(7):1694-1700).

By far most expression systems currently in use for making rotavirus capsid proteins are baculovirus-based expression systems. Methods for the production of highly immunogenic rotavirus capsid proteins in baculovirus-based expression systems have been e.g. described in the art (McGonigal T P et al., Virus Res. 1992; 23(1-2):135-150)

Furthermore, baculovirus expression systems and baculovirus expression vectors in general have been described extensively in textbooks (Baculovirus Expression Vectors, A Laboratory Manual. By David R. O'Reilly, Lois K. Miller, and Verne A. Luckow. Publisher: Oxford University Press, USA, May 1994; and Baculovirus and Insect Cell Expression Protocols. In: Methods in Molecular Biology™ Volume 388 (2007). Editors: David W. Murhammer).

Baculovirus-based expression systems are also commercially available, e.g. from Invitrogen Corporation, 1600 Faraday Avenue, Carlsbad, California 92008, USA. An alternative for Baculovirus-based expression systems are yeast-based expression systems. Yeast expression systems are e.g. described in: Production of recombinant proteins: novel microbial and eukaryotic expression systems by Gerd Gellissen, ISBN: 3-527-31036-3. Ready-to-use expression systems are i.a. commercially available from Research Corp. Technologies, 5210 East Williams Circle, Suite 240, Tucson, AZ 85711-4410 USA. Yeast and insect cell expression systems are also e.g. commercially available from Clontech Laboratories, Inc. 4030 Fabian Way, Palo Alto, California 94303-4607, USA. Alternatively, recombinant expression can be performed by using the AlphaVax® Alphavaccine Platform System technology using viral replicon particles (RP) based on a modified alphavirus.

Therefore, VP7 or fragments thereof can be obtained by heterologous expression of an ORF comprising the gene encoding the VP7 or a fragment thereof in a suitable expression system, such as a baculovirus expression system. Recombinant VP7 or fragments thereof can readily be made in large amounts and they are highly immunogenic.

Expression of recombinant VP7 or fragments thereof is of course also possible in mammalian cell-based expression systems as known in the art, but these systems would most likely be more expensive to use, when compared to the baculovirus-based expression systems.

The amount of recombinant VP7 in a vaccine is typically about 1 to 10 times, preferably 2 to 5 times, the amount used for whole virus vaccine. For example, Khodabandehloo et al., Iran J Public Health. 2012; 41(5): 73-84 reported an antibody titer for recombinant VP7, which is about four times lower compared to antibodies against the whole virus, which is explained with the additional presence of the immunogenic VP4 in the whole virus. Usually, an amount of between 1 and 100 µg of the recombinant VP7 would be very suitable as a vaccine dose. An amount of up to 500 µg could become necessary in case of using immunogenic fragments of VP7, wherein the amount necessary to achieve immunization depends on the length of the recombinant protein. From a point of view of costs, a preferred amount would be in the range of 1-50 µg of recombinant VP7, more preferred in the range of 1-25 µg. The route of administration would be comparable with that of inactivated whole virus particles.

A vaccine according to the invention on the basis of inactivated whole virus or recombinant VP7 or an immunogenic fragment thereof preferably comprises an adjuvant. Conventional adjuvants, well-known in the art are e.g. Freund's Complete and Incomplete adjuvant, vitamin E, non-ionic block polymers, muramyl dipeptides, Quill A®, mineral oil, e.g. Bayol® or Markol®, vegetable oil, and Carbopol® (a homopolymer), or Diluvac® Forte. The vaccine may also comprise a so-called "vehicle". A vehicle is a compound to which the polypeptide adheres, without being covalently bound to it. Often used vehicle compounds are e.g. aluminum hydroxide, -phosphate or -oxide, silica, Kaolin, and Bentonite.

In principle a vaccine according to the invention can be given just once. However, especially in the case of inactivated vaccines, be it whole virus vaccines, recombinant VP7 or immunogenic fragments, preferably a first and maybe even a second booster vaccination is given. A first booster would usually be given at least two weeks after the first vaccination. A very suitable moment for a booster vaccination is between 3 and 16 weeks after the first vaccination. A second booster, if necessary, would usually be given between 4 and 50 weeks after the first booster.

An alternative to the inactivated whole virus vaccine approach and the recombinant VP7 approach is the use of live recombinant non-rotavirus vectors that have pigs as their host animal, as carriers of the novel porcine RVB VP7 gene or an immunogenic fragment thereof.

Amongst the suitable recombinant non-rotavirus vectors that have pigs as their host animal, two vectors are especially suitable as carriers: Pseudorabies virus (PRV) and Classical Swine Fever Virus (CSFV). The use of such recombinant viruses in vaccines has the additional advantage that the vaccinated animals become at the same time vaccinated against both PRV and RVB or CSFV and RVB.

Live attenuated CSFV vectors are also very suitable as live recombinant vectors. Merely as an example; live attenuated CSFV from which the N<pro> gene has been deleted, has been described by Mayer et al (Immunochemical Methods in Cell and Molecular Biology, Academic Press, London, 1987). Such a live attenuated virus allows, i.a. at the site of the deletion of the N<pro> gene, for the insertion of the VP7 gene. Such a live recombinant CSFV vector equally forms a suitable carrier for the VP7 gene of the present invention.

The expression of the VP7 gene or a fragment thereof according to the invention can be brought under the control of any suitable heterologous promoter that is functional in a mammalian cell (see below). A heterologous promoter is a promoter that is not the promoter responsible for the transcription of the VP7 gene in the wild-type form of the novel porcine rotavirus according to the invention. It may be a rotavirus promoter responsible for the transcription of VP7 of another rotavirus, that does not belong to the virus according to the invention or it may be a non-rotavirus promoter.

Therefore, another embodiment of the present invention relates to a DNA fragment comprising a gene encoding a VP7 or a fragment thereof according to the invention, characterized in that said gene is under the control of a functional heterologous promoter. A promoter that is functional in a mammalian cell is a promoter that is capable of driving the transcription of a gene that is located downstream of the promoter in a mammalian cell.

Examples of suitable promoters that are functional in a mammalian cell include classic promoters such as the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well-known bovine growth hormone poly-adenylation sequence, the SV40 poly-adenylation sequence, the human cytomegalovirus (hCMV) terminator and poly-adenylation sequences.

Thus, another form of this embodiment relates to a vaccine for protecting a pig against an infection caused by RVB, characterized in that said vaccine comprises a live recombinant non-RVB vector comprising a DNA fragment comprising a gene encoding a VP7 or an immunogenic fragment thereof according to the invention under the control of a functional promoter and a pharmaceutically acceptable carrier.

Further, the live recombinant non-RVB vector should be expressing an immunogenically effective amount of VP7 or immunogenic fragment thereof.

An alternative for vaccination with an inactivated whole virus vaccine, a recombinant VP7 vaccine or a live recombinant non-RVB vector, is the use of DNA vaccination.

Such DNA vaccination is based upon the introduction of a DNA fragment carrying the gene encoding the VP7 according to the invention under the control of a suitable promoter, into the host animal. Once the DNA is taken up by the host's cells, the gene encoding the VP7 or fragment thereof is transcribed and the transcript is translated into VP7 in the host's cells. This closely mimics the natural infection process of the rotavirus. Suitable promoters are promoters that are functional in mammalian cells, as exemplified above.

A DNA fragment carrying the gene encoding the VP7 or fragment thereof under the control of a suitable promoter could e.g. be a plasmid. This plasmid may be in a circular or linear form.

Examples of successful DNA vaccination of pigs are i.a. the successful vaccination against Aujeszky's disease as described in Gerdts et al., Journal of General Virology 78: 2139-2146 (1997). They describe a DNA vaccine wherein a DNA fragment is used that carries glycoprotein C under the control of the major immediate early promoter of human cytomegalovirus. Vaccination was done four times with two weeks intervals with an amount of 50 μg of DNA. Vaccinated animals developed serum antibodies that recognized the respective antigen in an immunoblot and that exhibited neutralizing activity.

Another example of successful DNA vaccination of pigs is given by Gorres et al., Clinical Vaccine Immunology 18: 1987-1995 (2011). They described successful DNA vaccination of pigs against both pandemic and classical swine H1N1 influenza. They vaccinated with a prime vaccination and 2 homologous boosts at 3 and 6 weeks post priming, of a DNA vaccine comprising the HA gene of influenza H1N1 under the control of a functional promoter. Therefore, again another form of this embodiment relates to a vaccine for protecting a pig against an infection caused by RVB, characterized in that said vaccine comprises a DNA fragment comprising a VP7 gene or fragment thereof according to the present invention under the control of a functional promoter, and a pharmaceutically acceptable carrier.

Further, the DNA fragment comprising a gene encoding VP7 or fragment thereof according to the invention should be expressing an immunogenically effective amount of VP7 or immunogenic fragment thereof.

What constitutes an "immunogenically effective amount" of a vaccine according to the invention that is based upon a whole virus according to the invention, recombinant VP7 according to the invention, or immunogenic fragment thereof, a live recombinant vector or a DNA vaccine according to the invention depends on the desired effect and on the target organism. The term "immunogenically effective amount" as used herein relates to the amount of virus, recombinant protein, live recombinant vector or DNA vaccine that is necessary to induce an immune response in pigs to the extent that it decreases the pathological effects caused by infection with a wild-type rotavirus, when compared to the pathological effects caused by infection with a wild-type rotavirus in non-immunized pigs.

The determination whether a treatment is "immunologically effective", can be achieved, for instance, by administering an experimental challenge infection to vaccinated animals and next determining a target animal's clinical signs of disease, serological parameters or by measuring re-isolation of the pathogen, followed by comparison of these findings with those observed in field-infected pigs.

The amount of virus administered will depend on the route of administration, the presence of an adjuvant and the moment of administration.

A preferred amount of a live vaccine comprising virus according to the invention is expressed for instance as Tissue Culture Infectious Dose (TCID50). For instance, for a live virus a dose range between 10 and $10^9$ TCID50 per animal dose may advantageously be used, depending on the rest virulence of the virus. Preferably a range between $10^2$ and $10^6$ TCID50 is used.

Many ways of administration can be applied, all known in the art. Vaccines according to the invention are preferably administered to the animal via injection (intramuscular or via the intraperitoneal route) or per os.

The protocol for the administration can be optimized in accordance with standard vaccination practice. In all cases, administration through an intradermal injector (IDAL) is one way of administration. If a vaccine comprises inactivated virus or recombinant protein according to the invention, the dose would also be expressed as the number of virus particles to be administered. The dose would usually be somewhat higher when compared to the administration of live virus particles, because live virus particles replicate to a certain extent in the target animal, before they are removed by the immune system. For vaccines on the basis of inactivated virus, an amount of virus particles in the range of about $10^4$ to $10^9$ particles would usually be suitable. The amount may depend on the adjuvant used, but is typically within the defined range.

If a vaccine comprises recombinant protein according to the invention, the dose could also be expressed in micrograms of protein. For vaccines on the basis of recombinant protein, a suitable dose would usually be in the range between 1 and 500 micrograms of protein. The does, again, may depend on the adjuvant used.

If a vaccine comprises a DNA fragment comprising a gene encoding VP7, the dose would be expressed in micrograms of DNA. A suitable dose would usually be in the range between 5 and 500 micrograms of DNA. The dose may depend, i.a., on the efficiency of the expression plasmid used. Typically, an amount of between 20 and 50 micrograms of plasmid per animal would be sufficient for an effective vaccination.

A vaccine according to the invention may take any form that is suitable for administration in the context of pig farming, and that matches the desired route of application and desired effect. Preparation of a vaccine according to the invention is carried out by means conventional for the skilled person.

For oral administration the vaccine is preferably mixed with a suitable carrier for oral administration i.e. cellulose, food or a metabolisable substance such as alpha-cellulose or different oils of vegetable or animal origin.

In practice, swine are vaccinated against a number of pathogenic viruses or micro-organisms.

Therefore, it is highly attractive, both for practical and economic reasons, to combine a vaccine according to the invention for pigs with e.g. an additional immunogen of a virus or micro-organism pathogenic to pigs, or genetic information encoding an immunogen of said virus or micro-organism.

Thus, a preferred form of this embodiment relates to a vaccine according to the invention, wherein that vaccine comprises at least one other pig-pathogenic microorganism or pig-pathogenic virus and/or at least one other immunogenic component and/or genetic material encoding said other immunogenic component, of said pig-pathogenic microorganism or pig-pathogenic virus. An immunogen or immunogenic component is a compound that induces an immune response in an animal. It can e.g. be a whole virus or bacterium, or a protein or a sugar moiety of that virus or bacterium.

The most common pathogenic viruses and micro-organisms that are pathogenic for swine are *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

Therefore, a more preferred form of the invention relates to a vaccine according to the invention, wherein the virus or micro-organism pathogenic to swine is selected from the group of *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

Still another embodiment relates to a method for the preparation of a vaccine according to the invention, wherein the method comprises the mixing of a virus according to the invention and/or a recombinant protein according to the invention and/or a DNA fragment encoding a VP7 or a fragment thereof according to the invention and/or a live recombinant non-rotavirus vector encoding a VP7 or a fragment thereof according to the invention, and a pharmaceutically acceptable carrier.

In another embodiment, the present invention relates to a virus according to the invention and/or a recombinant protein and/or a VP7 or an immunogenic fragment thereof according to the invention and/or a DNA fragment encoding a VP7 or an immunogenic fragment thereof according to the invention and/or a live recombinant non-rotavirus vector encoding a VP7 or an immunogenic fragment thereof according to the invention, for use in a vaccine.

In another embodiment, the present invention relates to a method for the preparation of a vaccine as defined herein, characterized in that said method comprises the mixing of a virus, or an immunogenetically effective amount of a VP7 or of an immunogenic fragment thereof or a recombinant vector encoding the VP7 or the immunogenic fragment thereof, as defined herein, and a pharmaceutically acceptable carrier.

In another embodiment, the present invention relates to a virus, a DNA fragment, a VP7 or an immunogenic fragment thereof, or a recombinant vector encoding the VP7 or the immunogenic fragment thereof, as defined herein, for use in the manufacture of a vaccine for protecting a pig against an infection caused by porcine RVB.

As mentioned above, rotavirus infection is highly contagious. This means that it is important to know if rotavirus is present in a certain pig-population well before the first clinical signs become manifest. Thus, for efficient protection against disease, a quick and correct detection of the presence of rotavirus is important.

Therefore, it is another objective of this invention to provide diagnostic tools suitable for the detection of an infection of a virus according to the invention.

These tools partially rely on the availability of antibodies against the virus. Such antibodies can e.g. be used in diagnostic tests for rotavirus infection. Antibodies or antiserum comprising antibodies against the virus according to the invention can quickly and easily be obtained through vaccination of e.g. pigs, poultry or e.g. rabbits with the virus according to the invention followed, after about four weeks, by bleeding, centrifugation of the coagulated blood and decanting of the sera. Such methods are well-known in the art.

Other methods for the preparation of antibodies raised against the virus according to the invention, which may be polyclonal, monospecific or monoclonal (or derivatives thereof) are also well-known in the art. If polyclonal antibodies are desired, techniques for producing and processing polyclonal sera are well-known in the art for decades. Monoclonal antibodies, reactive against the virus according to the invention can be prepared by immunizing inbred mice by techniques also long known in the art.

Thus, another embodiment of the present invention relates to antibodies or antisera that are reactive with the virus according to the invention.

A diagnostic test kit based upon the detection of a virus according to the invention or antigenic material of that virus and therefore suitable for the detection of RVB infection may e.g. comprise a standard ELISA test. In one example of such a test the walls of the wells of an ELISA plate are coated with antibodies directed against the virus. After incubation with the material to be tested, labeled antibodies reactive with the virus are added to the wells. If the material to be tested would indeed comprise the novel virus according to the invention, this virus would bind to the antibodies coated to the wells of the ELISA. Labeled antibodies reactive with the virus that would subsequently be added to the wells would in turn bind to the virus and a color reaction would then reveal the presence of antigenic material of the virus.

Therefore, still another embodiment of the present invention relates to diagnostic test kits for the detection of a virus according to the invention or antigenic material of the virus, that comprise antibodies reactive with a virus according to the invention or with antigenic material thereof. Antigenic material of the virus is to be interpreted in a broad sense. It can be e.g. the virus in a disintegrated form, or viral envelope material comprising viral outer membrane proteins. As long as the material of the virus reacts with antiserum raised against the virus, the material is considered to be antigenic material.

A diagnostic test kit based upon the detection in serum of antibodies reactive with the virus according to the invention or antigenic material of the virus and therefore suitable for the detection of RVB infection may also e.g. comprise a standard ELISA test. In such a test the walls of the wells of an ELISA plate can e.g. be coated with the virus according to the invention or antigenic material thereof. After incubation with the material to be tested, e.g. serum of an animal suspected from being infected with the novel virus according to the invention, labeled antibodies reactive with the virus according to the invention are added to the wells. If antibodies against the novel virus according to the invention would be present in the tested serum, these antibodies will bind to the viruses coated to the wells of the ELISA. As a consequence, the later added labeled antibodies reactive with the virus would not bind and no color reaction would be found. A lack of color reaction would thus reveal the presence of antibodies reactive with the virus according to the invention.

Therefore, still another embodiment of the present invention relates to diagnostic test kits for the detection of antibodies reactive with the virus according to the invention or with antigenic material of the virus that comprise the virus according to the invention or antigenic material thereof.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemiluminescent-, radio-active- or dye molecules.

Suitable methods for the detection of antibodies reactive with a virus according to the present invention in the sample include, in addition to the ELISA mentioned above, immunofluorescence test (IFT) and Western blot analysis.

An alternative but quick and easy diagnostic test for diagnosing the presence or absence of a virus according to the invention is a PCR test as referred to above, comprising a PCR primer set reactive with a specific region of the VP7 DNA fragment of the novel virus according to the invention. Specific in this context means unique for e.g. the VP7 gene of the novel virus, i.e. not present in other members of the family of Reoviridae.

By simple computer-analysis of the novel VP7 gene sequence provided by the present invention with the known VP7 gene of other rotaviruses, the skilled person is able to develop specific PCR-primers for diagnostic tests for the detection of the novel virus and/or the discrimination between the novel virus and other viral (porcine) pathogens.

Thus, another embodiment relates to a diagnostic test kit for the detection of a virus according to the invention, characterized in that said test kit comprises a PCR primer set that is specifically reactive with a region of the VP7 gene sequence of the DNA fragment of the virus according to the invention.

EXAMPLES

Example 1: Identification of a New Rotavirus in Piglets

Recently, a neonatal diarrhea outbreak with clear clinical signs of rotavirus infection was observed in piglets in a farm of a large pork producer in Spain, although the sows were vaccinated against RVA.

Clinical symptoms observed in infected pigs were diarrhea at first week of live, with yellow feces of different consistency, sometimes liquid and sometimes thick feces. Piglets of primiparous and multiparous sows were affected. Morbidity was very high (40% of the litters in some batches), mortality 5-6%.

Due to diarrheal symptoms, pigs were vaccinated using Coliclos Prosystem® RCE (Merck Animal Health), a vaccine for use in swine as an aid in the prevention of rotaviral diarrhea, enterotoxemia and colibacillosis in nursing piglets, the vaccine containing two major Rotavirus A genotypes (G4, G5), four major *E. coli* pilus antigens and *C. perfringens* type C toxoid. Vaccination, however, did not result in disappearance of symptoms.

In particular, involvement of a virus was suspected because "feedback" of infected material resulted in immunity and disappearance of symptoms.

Maternal antibodies against RVA should have been present in the colostrum due to vaccination. Samples were sent for laboratory analysis, without a plausible explanation of the rotavirus signs despite the vaccination regime.

Samples were collected by taking rectal swabs, from subjects including 6 groups of sows with having clear rota clinical signs (the "rota groups"), and of 3 groups having no signs ("control groups". From each group, rectal swabs were taken from the sow and three piglets. The samples were analyzed for the presence of viruses by VIDISCA (Virus discovery based on cDNA-AFLP (amplified fragment length polymorphism), a method originally described by van der Hoek et al., (Nat Med. 2004; 10:368-373). Virus discovery based on VIDISCA is a novel approach that provides a fast and effective tool for amplification of unknown genomes, e.g., of human pathogenic viruses. The VIDISCA method is based on double restriction enzyme processing of a target sequence and ligation of oligonucleotide adaptors that subsequently serve as priming sites for amplification. As the method is based on the common presence of restriction sites, it results in the generation of reproducible, species-specific amplification patterns. The method allows amplification and identification of viral RNA/DNA, with a lower cutoff value of 10(5) copies/ml for DNA viruses and 10(6) copies/ml for the RNA viruses.

Using the VIDISCA method, the nucleotide sequence of SEQ ID No. 1 and having the amino acid sequence of SEQ ID No. 2 belonging to a VP7 protein of an unknown rotavirus was detected in 5 of the 6 sows of the "rota groups" at a high level. Of these sows, each of the 3 piglets also had high levels of virus presence indicative for viremia. In the piglets of the 6$^{th}$ sow, only low levels of the virus could be detected, around detection level. In 2 of the "control groups" the virus could not be found. In the other control group the virus could be found at a very low level in 2 out of the 3 tested piglets, around detection level. The other animals (sow and piglet) in this group were found to be negative for the virus. All rectal swabs of all tested animals were free of any other rota virus. This means that the newly found rota virus must have been responsible for the induction of rota induced disease. Phylogenetic analysis revealed that this novel virus belongs to a rotavirus B within the G12 genotype of rotavirus B (see FIG. 1; the new virus indicated as "New RotaB VP7 Spain"). Rotaviruses of this genotype have not been unambiguously found to be disease causing in the art. It is believed that the new strain is a representative of a new pathogenic sub-genus within the genus G12.

In addition, the entire coding regions of the eleven different proteins (1 protein per segment) was obtained by Illumina sequencing, revealing the sequences of SEQ ID NO. 1-22 of the new rotavirus. For the proteins of segments 2-11, sequences of the full-length coding regions, i.e. from start to stop, were obtained. For the protein of segment 1, the sequence of the partial coding region was obtained.

Genome assembly was from sequencing information obtained from serum samples. Illumina sequencing was performed as follows:

Sample "I18-45_Serum-nr-49 Sow D3004 Spain" was used for library preparation and sequencing of the segments. One hundred and ten µl of material was spun down for 10 minutes at 10,000×g and treated with TurboDNase (Thermofisher) as described (de Vries M, et al. PLoS One. 2011; 6(1):e16118. doi:10.1371/journal.pone.0016118), after which nucleic acids were extracted by Boom extraction method (Boom R, et al. J Clin Microbiol. 1990; 28(3):495-503). The samples were sheared using dsDNA Fragmentase (New England Biolabs). The sheared samples were purified with AMPure XP beads (agencourt AMPure XP PCR, Beckman Coulter) in a ratio 1:1.8 (sample:beads) to remove the enzymes. After purification the samples were end repaired with DNA polymerase I, Large (Klenow) Fragment (New England Biolabs). The end repaired samples were purified with AMPure XP beads in a ratio 1:1.8 (sample:beads) to remove the enzymes, after which the samples were A-tailed by using Klenow Fragment (3'-5' Exo-) (New England Biolabs). The samples were purified with AMPure XP beads in a ratio 1:1.8 (sample:beads) to remove the polymerases. Bubble adaptors from the NEBNext Multiplex Oligos for Illumina (New England Biolabs) were ligated to the A-tailed samples, by use of T4 ligase. A size selection was performed by use of AMPure XP beads first in a ratio 1:0.5 (sample:beads) to ensure that most fragments with a size bigger than 400 bp were removed, followed by adding additional AMPure XP beads to the supernatant to get to a final ratio of 1:0.85 (sample:beads) to bind DNA fragments between 200-400 bp and to remove fragments smaller than 200 bp. After the size selection the Bubble adaptors were opened by using USER enzyme from the NEBNext Multiplex Oligos for Illumina (New England Biolabs). Next, a 28 cycle PCR was performed with adaptor specific primers from the NEBNext Multiplex Oligos for Illumina (New England Biolabs) and Q5 hotstart mastermix (New England Biolabs); 30 sec 98° C., and cycles of 10 sec 98° C. and 75 sec 65° C., followed by 5 min 65° C. After PCR the samples underwent size selections by use of AMPure XP beads in a ratio 1:0.5 (sample:beads) to remove fragments with a size bigger than 400 bp, and to the supernatant additional AMPure XP beads were added to get to a final ratio of 1:0.85 (sample:beads) to bind DNA fragments between 200-400 bp and to remove fragments smaller than 200 bp. Next the concentration of the DNA was measured via Qubit dsDNA HS Assay Kit (Thermofisher), the size was checked on the bioanalyzer with a High Sensitivity DNA Analysis Kit. The library was sequenced by use of the MiSeq (Illumina) using paired end sequencing and the v2 kit (Illumina) Quality control and trimming is done with Trimmomatic 0.35 with the following settings (phred 33, LEADING:3 TRAILING:3 SLIDING-WINDOW:4:15 MINLEN:36) and assembly is done with SPAdes version 3.5.0-Darwin, with the following settings (—"careful"-"only-assembler"-"paired reads"). To have the terminal sequences of the segments (5' and 3') the de novo assembled contigs were aligned to segments 1 to 11 of KR052709.1, KR052710.1, KR052711.1, KR052712.1, KR052713.1, KR052714.1, KR052715.1, KR052716.1, KR052717.1, KR052718.1, KR052719.1 respectively. All assembled sequenced were checked by eye for quality by aligning to the closest relatives of each segment: AB673232.1; KF882541.1; KR052716.1; KR052717.1; KX869737.1; KX362400.1; KX869732.1; KX869733.1; KX869735.1; MG272043.1; MG272114.1.

Example 2: Isolation of the New Rotavirus and Reinfection of Piglets with the New Rotavirus Introduction The objective of this study was to propagate the novel group B rotavirus (novel RVB) field isolate of example 1 in caesarean derived, colostrum deprived (CD/CD) piglets.

The study was performed to confirm infectivity of the newly discovered virus. An animal passage of the infectious virus should result in virus with maintained virulence and high titers in the intestinal contents. In addition to that, clinical symptoms observed at the farm from which the virus originated, diarrhea, should be reproduced.

Cesarean delivery and colostrum deprivation are needed to prevent the piglets from acquiring interfering maternally derived antibodies against rotaviruses, or to become infected with rotavirus or any other virus during farrowing. Natural or other human-aided means of delivery have higher chances of unintentional infection of the piglets, which would interfere with the study.

The piglets were infected on 3 days of age since older piglets are less susceptible to a rotavirus infection. An early infection likely results in systemic viremia and infection of the gastrointestinal tract, rather than solely an infection of the gastrointestinal tract.

Materials and Methods

For this study 5 CD/CD piglets were used. Piglets were numbered and transported to the experimental facility. For transportation, piglets were placed in specific pathogen free transport containers, and subsequently transported in a climate controlled, animal transportation vehicle. Upon arrival at the experimental facility, piglets were housed in an isolation room.

At 3 days of age (study day 0), piglets were intragastrically infected with 5 mL inoculum per piglet of the novel RVB isolate composed of fecal-derived virus obtained in Example 1.

For the preparation of infectious material, fecal contents of 7 piglets (from 3 different sows) carrying the identical novel RVB were pooled (total volume 12 mL). To activate the virus, trypsin was added to a final concentration of 2 U/mL. The material was incubated for 30 mins at 37° C., after which the volume was increased to 30 mL using EMEM-medium.

The quantity of RVB in the pooled sample was $2.26*10^7$ copies/µl based on a titration series of a plasmid containing the amplicon with known concentrations. The inoculum also contained an astrovirus, for which a qPCR diagnostic assay was set up, but without a standard curve. The Ct value of the inoculum sample was 32.75

Five (5) mLs of the inoculum were administered intragastrically per piglet using a syringe and feeding tube/urethral catheter. After applying the inoculum, 2 mLs of air were gently pushed in through the gastric tube using a syringe to empty the content of the tube completely. If necessary, the mouth of the piglet was wiped off with a paper towel containing 70% ethanol after inoculation.

Starting from the day of challenge until 3 days post infection, all piglets were observed for clinical signs of diarrhea. Prior to and following infection, individual feces samples were collected from all piglets once per day directly from the rectal opening. In case that was not successful, rectal swab samples were collected. All feces samples/rectal swab were stored immediately at −70° C. At day 3 post infection (72 h), piglets were necropsied. During necropsy, contents of the intestines and scrapings of jejunum, ileum, colon and caecum tissues were collected as two pooled samples per piglet. In addition, a small tissue sample was taken from jejunum, ileum, caecum and colon for (immune) histochemistry.

The piglets were fed Swinco opticare 2100 milk until study day 0. From study day 0 until the end of the experiment (study day 3) the piglets were fed with Swinco opticare milk Silver.

qPCR

Reverse Transcription quantitative PCR (RT-qPCR) was performed on the fecal samples.

Nucleic Acids (NA) were extracted using the Magnapure methodology (Roche).

A specific RT-qPCR for the novel Rota B virus was performed on the NA extracts.

```
Forward primer,:
                                    (SEQ ID NO: 23)
5'-CAGACGATCTGATAGGGATGTATTG-3'.

Reverse primer:
                                    (SEQ ID NO: 24)
5'-ATGTCCGTGACGTAGTATCTTC-3'.
``` qPCR protocol: 5 min 55° C., 5 min 95° C., [10 sec 94° C., 25 sec 58° C.]×39

The kit used for performing the qPCR was the Invitrogen SuperScript™ III Platinum™ One-Step qRT-PCR Kit. A quantitation was performed based on a titration series of a plasmid containing the amplicon with known concentrations.

An astrovirus specific RT-qPCR was performed on the NA extracts.

```
Forward primer:
                                    (SEQ ID NO: 25)
5'-GTGCAGATGTGTTGGCGTATAAG-3'

Reverse primer:
                                    (SEQ ID NO: 26)
5'-TGAAGCGTACAAACCAGGATGAG-3'
``` qPCR protocol: 3 min 55° C., 5 min 95° C., [15 sec 95° C., 30 sec 60° C.]×39

The kit used for performing the qPCR was the Invitrogen SuperScript™ III Platinum™ One-Step qRT-PCR Kit, catalog nr. 11732020. No quantitation based on a titration series was performed.

Results

The health status of all animals was monitored throughout the animal study. At 21 h post infection, piglets were first diagnosed with symptoms of diarrhea and decreased appetite. All piglets developed clinical symptoms similar to those observed on the index farm.

TABLE 1

Progression of clinical symptoms at different hours post infection (pi):

| Piglet, Nr. | 21 h pi | 33 h pi | 45 h pi | 48 h pi | 58 pi | 68 h |
|---|---|---|---|---|---|---|
| 1 | Diarrhea, decreased appetite | Diarrhea | Diarrhea, decreased appetite | Diarrhea, decreased appetite, sluggish, slightly dehydrated | Diarrhea, decreased appetite, sluggish, | Diarrhea, decreased appetite, sluggish, |
| 2 | Diarrhea, decreased appetite | Diarrhea | Diarrhea, decreased appetite | Diarrhea, decreased appetite, sluggish, slightly dehydrated | Diarrhea, decreased appetite, sluggish | Diarrhea, decreased appetite, sluggish |
| 3 | Diarrhea, decreased appetite | Diarrhea | Diarrhea, decreased appetite | Diarrhea, decreased appetite, sluggish, dehydrated | Diarrhea, decreased appetite, sluggish, dehydrated | Diarrhea, decreased appetite, sluggish |
| 4 | Diarrhea, decreased appetite | Diarrhea | Diarrhea, decreased appetite | Diarrhea, decreased appetite | Diarrhea, decreased appetite | Diarrhea, decreased appetite |
| 5 | Diarrhea, decreased appetite | Diarrhea | Diarrhea, decreased appetite | Diarrhea, decreased appetite, sluggish, slightly dehydrated | Diarrhea, decreased appetite, sluggish | Diarrhea, decreased appetite, sluggish | qPCR Quantification of RVB:

Nucleic acids were extracted from all fecal samples collected during the study and screened for the presence of RVB with an RVB-specific qPCR. The results are presented in Table 1 below:

| Piglet # | Sample type | Fecal inoculum | 0 hpi | 24 hpi | 48 hpi | 72 hpi |
|---|---|---|---|---|---|---|
| 1 | Rectal swab | 2.26E+07 | 0.00E+00 | 1.79E+06 | 2.71E+04 | 6.43E+05 |
| 2 | Rectal swab | 2.26E+07 | 0.00E+00 | 1.71E+07 | 8.23E+05 | 9.80E+05 |
| 3 | Rectal swab | 2.26E+07 | 0.00E+00 | 6.30E+05 | 5.52E+05 | 1.09E+04 |
| 4 | Rectal swab | 2.26E+07 | 0.00E+00 | 2.95E+05 | | 8.50E+04 |
| 5 | Rectal swab | 2.26E+07 | 0.00E+00 | 1.58E+06 | 2.65E+05 | 5.05E+04 |

No RVB was present in the fecal samples of the piglets at the start of the study. At 24 h post infection, RVB could be detected in the feces of the infected piglets. The RVB remained present in the samples taken on the following days. The sample of piglet 4 taken at 48 h was not available for analysis.

The analysis of feces or fecal swabs during the study was semi-quantitative. The feces become more watery during progression of clinical symptoms. Feces were not collected in quantified amounts.

Subsequently, a qPCR quantification of astrovirus was performed on all samples to make sure this virus, which was present in the inoculum in low concentrations as diagnosed with Next Generation Sequencing and verified using qPCR, did not have an effect on the animals during the animal study.

All fecal samples collected during the study were analysed for astrovirus presence using qPCR, but none of the fecal samples were found positive for astrovirus. Thus, no replication of this virus could be shown.

In conclusion, in vivo infectivity, replication and pathogenicity of the novel Rota B virus was confirmed in this study.

Thus, the present invention relates to the following embodiments:

1. An isolated rotavirus which is a member of the subspecies of porcine group B rotaviruses genotype G12, which in its wild type form causes diarrhea in pigs, said virus being characterized in that it has a viral genome comprising an open reading frame having a nucleotide sequence corresponding to the nucleotide sequence depicted in SEQ ID NO: 1 or a nucleotide sequence having a level of identity of at least 90% therewith.

2. The isolated virus according to embodiment 1, characterized in that the nucleotide sequence having a level of identity of at least 90% to the nucleotide sequence depicted in SEQ ID NO: 1 encodes an outer viral capsid glycoprotein VP7.

3. A nucleic acid fragment comprising an open reading frame comprising at least 100 nucleotides, characterized in that said nucleic fragment has a nucleotide sequence that corresponds to a sequence having a level of identity of at least 90% to the nucleotide sequence depicted in SEQ ID NO: 1.

4. The nucleic acid fragment according to embodiment 3, characterized in that the open reading frame encodes an outer viral capsid glycoprotein VP7.

5. The nucleic acid fragment according to embodiment 3 or 4, characterized in that the open reading frame is under the control of a heterologous promoter.

6. A recombinant protein encoded by the nucleic acid fragment according to any one of embodiments 3 to 5.

7. An outer viral capsid glycoprotein VP7 or a fragment thereof, characterized that it is encoded by a nucleic acid fragment according to any one of embodiments 3 to 5.

8. An outer viral capsid glycoprotein VP7 or a fragment thereof, characterized that it is a protein according to SEQ ID NO:2, or a protein having a level of identity of at least 90% therewith.

9. A vaccine for use in protecting against an infection caused by porcine group B rotavirus, characterized in that said vaccine comprises an immunogenically effective amount of a virus according to any one of embodiments 1 and 2, or an immunologically effective amount of a recombinant protein according to embodiment 6, or an immunologically effective amount of an outer viral capsid glycoprotein VP7 according to embodiments 7 or 8, or a nucleic acid fragment according to any of the embodiments 3 to 5, and a pharmaceutically acceptable carrier.

10. The vaccine according to embodiment 9 for use in prophylactically treating an animal.

11. An antibody or antiserum reactive with a virus according to any one of embodiments 1 to 2 or with a recombinant protein according to embodiment 6 or with an outer viral capsid glycoprotein VP7 according to embodiment 7 or 8.

12. A diagnostic test kit for the detection of antibodies reactive with a virus according to any one of embodiments 1 to 2, or with antigenic material thereof, or reactive with an outer viral capsid glycoprotein VP7 according to embodiment 7, characterized in that said test kit comprises a virus according to any one of embodiments 1 to 2 or antigenic material thereof or a recombinant protein according to embodiment 6 an outer viral capsid glycoprotein VP7 according to embodiments 7 or 8.

13. A diagnostic test kit for the detection of a virus according to any one of embodiments 1 to 2, or antigenic material thereof, or an outer viral capsid glycoprotein VP7 according to embodiments 7 or 8, characterized in that said test kit comprises antibodies reactive with a virus according to any one of embodiments 1 to 2 or antigenic material thereof or reactive with a recombinant protein according to embodiments 6 or reactive with an outer viral capsid glycoprotein VP7 according to embodiment 7 or 8.

14. A method for protecting an animal against an infection caused by porcine group B rotavirus by systemically administering a vaccine according to embodiment 9 or 10 to the animal.

15. The method according to embodiment 14, characterized in that said method comprises the mixing of a virus according to any one of embodiments 1 and 2, or a recombinant protein according to embodiment 6, or an outer viral capsid glycoprotein VP7 according to embodiments 7 or 8, or a nucleic acid fragment according to any of the embodiments 3 to 5, and a pharmaceutically acceptable carrier.

16. A virus according to any one of embodiments 1 and 2, or a recombinant protein according to embodiment 6, or an outer viral capsid glycoprotein VP7 according to embodiments 7 or 8, or a nucleic acid fragment according to any of the embodiments 3 to 5, for use in the manufacture of a vaccine for protecting an animal against an infection caused by porcine group B rotavirus.

The invention claimed is:

1. An isolated rotavirus which is a member of the subspecies of porcine group B rotaviruses genotype G12, which in its wild type form causes diarrhea in pigs, said virus being characterized in that it has a viral genome comprising an open reading frame having a nucleotide sequence corresponding to the nucleotide sequence depicted in SEQ ID NO: 1 or a nucleotide sequence having a level of identity of at least 90% therewith.

2. The isolated virus according to claim 1, characterized in that the nucleotide sequence having a level of identity of at least 90% to the nucleotide sequence depicted in SEQ ID NO: 1 encodes an outer viral capsid glycoprotein VP7.

3. A nucleic acid fragment comprising an open reading frame, said open reading frame comprising at least 200 nucleotides, characterized in that said nucleic acid fragment has a nucleotide sequence that corresponds to a sequence having a level of identity of at least 90% to the nucleotide sequence depicted in SEQ ID NO: 1.

4. The nucleic acid fragment according to claim 3, characterized in that the open reading frame encodes an outer viral capsid glycoprotein VP7.

5. The nucleic acid fragment according to claim 3, characterized in that the open reading frame is under the control of a heterologous promoter.

6. A recombinant protein encoded by the open reading frame of the nucleic acid fragment according to claim 3.

7. An outer viral capsid glycoprotein VP7 or a fragment thereof, characterized that it is a protein according to SEQ ID NO:2, or a protein having a level of identity of at least 93% therewith.

8. A vaccine for use in protecting against an infection caused by porcine group B rotavirus, characterized in that said vaccine comprises an immunogenically effective amount of a virus according to claim 1, and a pharmaceutically acceptable carrier.

9. A vaccine for use in protecting against an infection caused by porcine group B rotavirus, characterized in that said vaccine comprises an immunogenically effective amount of a virus according to according to claim 6 and a pharmaceutically acceptable carrier.

10. A vaccine for use in protecting against an infection caused by porcine group B rotavirus, characterized in that said vaccine comprises an immunogenically effective amount an outer viral capsid glycoprotein VP7 according to claim 7.

11. A method for protecting an animal against an infection caused by porcine group B rotavirus by systemically administering a vaccine according to claim 8 to the animal.

12. A virus according to claim 1 for use in the manufacture of a vaccine for protecting an animal against an infection caused by porcine group B rotavirus.

13. A recombinant protein according to claim 6 for use in the manufacture of a vaccine for protecting an animal against an infection caused by porcine group B rotavirus.

14. An outer viral capsid glycoprotein VP7 according to claim 7 for use in the manufacture of a vaccine for protecting an animal against an infection caused by porcine group B rotavirus.

15. A nucleic acid fragment according to any of the claim 3 for use in the manufacture of a vaccine for protecting an animal against an infection caused by porcine group B rotavirus.

16. A vaccine for use in protecting against an infection caused by porcine group B rotavirus, characterized in that said vaccine comprises a nucleic acid fragment according to claim 3 and a pharmaceutically acceptable carrier.

17. A method for protecting an animal against an infection caused by porcine group B rotavirus by systemically administering a vaccine according to claim 16 to the animal.

18. A method for protecting an animal against an infection caused by porcine group B rotavirus by systemically administering a vaccine according to claim 9 to the animal.

19. A method for protecting an animal against an infection caused by porcine group B rotavirus by systemically administering a vaccine according to claim 10 to the animal.

* * * * *

SEQUENCE LISTING

<160> NUMBER OF SEQ ID NOS: 26

<210> SEQ ID NO 1
<211> LENGTH: 809
<212> TYPE: DNA
<213> ORGANISM: Unknown
<220> FEATURE:
<223> OTHER INFORMATION: Description of Unknown:
      Reoviridae family sequence

<400> SEQUENCE: 1

```
gcataaaatg gcgttaacgc tgcttctcgt ccttgctgct tgcgctaatg cacaattgaa      60
tgttattcca gcaactgatc ctgaaatatg catactatat gctgatgata tgaatgacgc     120
gaaacaatat tttgggaatt ttacagagat ttttgaaagt tataatcacg taactataag     180
ctttacgaac tattcatccg ataactatga cgttattgaa atcttatcca aatataacta     240
tgatgcctgc gatatactag ccatttatgt aaagtatgag tatatggatt ttgcaacttt     300
tctgcaatct gaaaacaact gttccaaatt tgcaggtggg aaaattcact atgtgcaatt     360
accaagagac caagaatggt tcgtgtattc aaaagatctc aagttttgtc cattgtcaga     420
cgatctgata gggatgtatt gtgatacaca attatctggg acctattttg aggtagctcc     480
aaacagaaga tactacgtca cggacatccc agaattcact agtaaaggtt acaccttata     540
ttctaacaat ccattttacg tatgtcaaag aatcacagaa aacccatgga ttaacgtaca     600
ttatttttat gctggcaatg aaccatcagg gacaatttct aaacgaataa gttggggtaa     660
tgtctggaca aatgtcacaa cattcgcgca aatgttatat aaaatattag atatattctt     720
caatagtagt agaagtgctc aaccgcgagc ttaaagagga ctaggcgaaa gggaggaaac     780
caaacgagta gctgaagcaa ataaaaacc                                        809
```

<210> SEQ ID NO 2
<211> LENGTH: 248
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP7

<400> SEQUENCE: 2

```
Met Ala Leu Thr Leu Leu Leu Val Leu Ala Ala Cys Ala Asn Ala Gln
1               5                   10                  15
```

```
Leu Asn Val Ile Pro Ala Thr Asp Pro Glu Ile Cys Ile Leu Tyr Ala
            20                  25                  30

Asp Asp Met Asn Asp Ala Lys Gln Tyr Phe Gly Asn Phe Thr Glu Ile
        35                  40                  45

Phe Glu Ser Tyr Asn His Val Thr Ile Ser Phe Thr Asn Tyr Ser Ser
 50                  55                  60

Asp Asn Tyr Asp Val Ile Glu Ile Leu Ser Lys Tyr Asn Tyr Asp Ala
 65                  70                  75                  80

Cys Asp Ile Leu Ala Ile Tyr Val Lys Tyr Glu Tyr Met Asp Phe Ala
                85                  90                  95

Thr Phe Leu Gln Ser Glu Asn Asn Cys Ser Lys Phe Ala Gly Gly Lys
            100                 105                 110

Ile His Tyr Val Gln Leu Pro Arg Asp Gln Glu Trp Phe Val Tyr Ser
        115                 120                 125

Lys Asp Leu Lys Phe Cys Pro Leu Ser Asp Asp Leu Ile Gly Met Tyr
130                 135                 140

Cys Asp Thr Gln Leu Ser Gly Thr Tyr Phe Glu Val Ala Pro Asn Arg
145                 150                 155                 160

Arg Tyr Tyr Val Thr Asp Ile Pro Glu Phe Thr Ser Lys Gly Tyr Thr
                165                 170                 175

Leu Tyr Ser Asn Asn Pro Phe Tyr Val Cys Gln Arg Ile Thr Glu Asn
            180                 185                 190

Pro Trp Ile Asn Val His Tyr Phe Tyr Ala Gly Asn Glu Pro Ser Gly
        195                 200                 205

Thr Ile Ser Lys Arg Ile Ser Trp Gly Asn Val Trp Thr Asn Val Thr
    210                 215                 220

Thr Phe Ala Gln Met Leu Tyr Lys Ile Leu Asp Ile Phe Phe Asn Ser
225                 230                 235                 240

Ser Arg Ser Ala Gln Pro Arg Ala
                245

<210> SEQ ID NO 3
<211> LENGTH: 3442
<212> TYPE: DNA
<213> ORGANISM: Unknown
<220> FEATURE:
<223> OTHER INFORMATION: Description of Unknown:
      Reoviridae family sequence

<400> SEQUENCE: 3
ccagcttagt gtatacaaat ccaaaggtag caatagttca attcaccaga actgataacg      60
aaaaattatg gcagtcaaaa gaattgaacg tgttatyacc agtagaatta ctaacgcaac     120 taagaatga actagataga gcaaaaacgc tagatgaaaa aattgaaata cttttaagat     180
taagatactt cactgtatat gtcgaagaca atctgataa aagatcaatt atatcaagct      240
ggctaagaaa aactataaca gaattgggtg atgaacccga gtttgagtca atacaactca     300
ttgaacatca agctcgacaa tggaaaatcg acaacgcagg ctctctaaga gcatatcatc     360
acaacatccc tatcaatgaa ttcattcgtg ataatgaaat tgaataatt gacacaggag      420 attataaatg gaagtcggac acactggcag gattaaaccc aaactattat cacagaacgc     480
acacgttaat tgggtcagtt cttttcgcga ttcactcaag acttaaattc tatactggag     540
acaaaaaaag agcacttgca tatttgttaa aggtaataga acaatgttat tcccagggct     600
atcttgaatt atcaagaaat agaaaatggt ctcacactat caatgaattg cgcaagtcta     660
```

-continued

```
attttagatt atataatgca aaagtgatac atgcggcatg cgctatgata tccctactac    720
atgcggatcc gatcaacgca gaattcttat gtcaaataat tgcagtgtac cagatcatgc    780
cttcacatgc agcaaaagta ttgtcatctc cgatgacgtt atatgtaggt atcgcaacct    840
tcccatccag acaagtaata tcaactggta atgcttcaga gtgtgccccg acatcgaatc    900
caaataacac ttttgttgct gaatcacaaa agaatgtatg gcgtgaagct tataagaatg    960
atcctctgaa tcactccaaa atgttagaga ttatgaatct gaatctaaca acaaacgttg   1020
gaactttctc actgatattt aattgttttt cagcaacgtt tcatgttggc catagagtag   1080
acaatgccca agatgctata acagaacaag tttcagttaa atacacctca gatgttgaca   1140 agaaatgta tgacacatac tactataaat tgaaacaaat gctgaaagac gaaattattc   1200
agtatgtgga agaacacata gcaaagaact atagggacgt aactgcagaa tctttgtcag   1260
ctctagccaa ttcatcaaac ggattcatta agaagttga gtttgtggat agaaaaataa   1320
aaacgacgaa gaagatttta catctcgatt ctgacttgat ttcaaataca tacagtgacc   1380
ttactaaatc actatcacat gggataccaa tgggtaccag aaacgttcca gctagacaaa   1440
cgagaggtat tttcatatta ccttggcaag tggcggccat tcaacataca attgcagagt   1500
cattatacaa aagagcaaaa aaaggagcat atggaggatc gtttgctgaa gcgtatacag   1560
caaaaaccgc ttctttaact tatggtgtgt tagctgaaga tacgtcaaaa gcaatgagga   1620
tcatacttta tactgatgtg tctcaatggg atgctagtca acataacact gtgccatacc   1680
gttcggcatg gataaatgct atacgtgaag cgagatcgga attacgctgg aactattcag   1740
atgaaccata cgttttaggt atgaatgttt tagacaatat ggttaagata caagaatatc   1800
tactaaactc taacctggtt gtatcatctc caggatcatt gagaccaaca aaaatcattc   1860
gataccatgg tgtagcctct ggtgagaaaa ctacaaaaat tggaaaattca tttgcaaacg   1920 ttgcattgat cgaaacagtc ctagactata caaaacaaca aataccagat cttgaaattt   1980
cacatctaag agttgacggt gacgacaatg ttgtaactat taatacatca tgtccaattg   2040
agagattaca agccataatt aaaaacaact actcgaagtt aaacgctaga gtgaaagcac   2100
tagcatcata tacaggactc gaaatggcaa agagatttgt tgtatgcggc aaaatatttg   2160
agagaggtgc gattccaata tttactgctg aaaggcccta tggtacagat ctatcaacac   2220
agtctatgtg tggatcttca atctattcaa cggccgtaaa cgcatatcga gggtttggcg   2280
atgaatattt ttcatttatg ctagatgtac tggttccacc ttcatcatca gttagagtca   2340
cagggagatt acgagtgttg ttatcaccag ttacattata tgcgactggt cctttaagct   2400
ttgaagttac gccgcaaggt ttaggaggta gaggaagaat gttcacagaa tctaaaaaat   2460
tgttcacact atttaaatta cttacacaaa cagtatcagt gtcggtcacg ccagaggata   2520
tcaaaaaata ttcagctact aaacagttta atgcgcgaac tgacgtcatg attaaaagca   2580
tgcgtgagag agtaggtggg gatgcaaagg cattaaacag aataatgatt gacaaggaag   2640
aacagaagac tctaggtgta ccgaacgttt taagtcaaaa aaatagagat caagtatcac   2700
aagctatcaa aatacttggt gtacctgaac gagacgatct ttcaacgtca ggatattacc   2760
cagaagaact ttactcattg gttatacaac actcagttgt taagtacatg gattacggtg   2820
ttcagcattc aatctataat gtgaactgtg aaccagtgaa attactacat gcccagttgg   2880
gaatacgcat ttctgattca aaaccaatcg caaagccagt taatcattta tacgacattg   2940
tcagttcgat ttctccaatc agaatttctc caagtgattt aatcaaacaa gctcgcgagt   3000
acaatctgac gtcgtataaa gggaaaaggg aattttttgtt agatttaggt ttaaatggta   3060
```

```
acactctgaa aacatattta gcttccaaac tacttttag agatcttatg ctgtccaagt    3120
atgatgagct atactctact ccaggattcg gcgcgacaca attaacaaca atcccactgg    3180
acatttcgtc agcggaaaaa atcttctctc taactcttaa attgccagct cacttgtatg    3240
aagtagtcat gctgctgttg ttatatgaat atgtacattt cgttttgca tgtaagagga     3300 cctttacggc gacactacat attacttcac aggatgacgc tgccaaatta accaaacaga    3360
tactacaaat gttagatgac attaagttgg ataaggtttc atttaaagat gaagcctggt    3420
agatcatatc cacataaaaa cc                                             3442
```

<210> SEQ ID NO 4
<211> LENGTH: 1139
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP1 Pol
<220> FEATURE:
<221> NAME/KEY: MOD_RES
<222> LOCATION: (32)..(32)
<223> OTHER INFORMATION: Any amino acid

<400> SEQUENCE: 4

```
Ser Leu Val Tyr Thr Asn Pro Lys Val Ala Ile Val Gln Phe Thr Arg
1               5                   10                  15

Thr Asp Asn Glu Lys Leu Trp Gln Ser Lys Glu Leu Asn Val Leu Xaa
            20                  25                  30

Pro Val Glu Leu Leu Thr Gln Leu Lys Asn Glu Leu Asp Arg Ala Lys
        35                  40                  45

Thr Leu Asp Glu Lys Ile Glu Ile Leu Leu Arg Leu Arg Tyr Phe Thr
    50                  55                  60

Val Tyr Val Glu Asp Lys Ser Asp Lys Arg Ser Ile Ile Ser Ser Trp
65                  70                  75                  80

Leu Arg Lys Thr Ile Thr Glu Leu Gly Asp Glu Pro Glu Phe Glu Ser
                85                  90                  95

Ile Gln Leu Ile Glu His Gln Ala Arg Gln Trp Lys Ile Asp Asn Ala
            100                 105                 110

Gly Ser Leu Arg Ala Tyr His His Asn Ile Pro Ile Asn Glu Phe Ile
        115                 120                 125

Arg Asp Asn Glu Ile Glu Ile Ile Asp Thr Gly Asp Tyr Lys Trp Lys
    130                 135                 140

Ser Asp Thr Leu Ala Gly Leu Asn Pro Asn Tyr Tyr His Arg Thr His
145                 150                 155                 160

Thr Leu Ile Gly Ser Val Leu Phe Ala Ile His Ser Arg Leu Lys Phe
                165                 170                 175

Tyr Thr Gly Asp Lys Lys Arg Ala Leu Ala Tyr Leu Leu Lys Val Ile
            180                 185                 190

Glu Gln Cys Tyr Ser Gln Gly Tyr Leu Glu Leu Ser Arg Asn Arg Lys
        195                 200                 205

Trp Ser His Thr Ile Asn Glu Leu Arg Lys Ser Asn Phe Arg Leu Tyr
    210                 215                 220

Asn Ala Lys Val Ile His Ala Ala Cys Ala Met Ile Ser Leu Leu His
225                 230                 235                 240

Ala Asp Pro Ile Asn Ala Glu Phe Leu Cys Gln Ile Ile Ala Val Tyr
                245                 250                 255
```

```
Gln Ile Met Pro Ser His Ala Ala Lys Val Leu Ser Ser Pro Met Thr
            260                 265                 270

Leu Tyr Val Gly Ile Ala Thr Phe Pro Ser Arg Gln Val Ile Ser Thr
            275                 280                 285

Gly Asn Ala Ser Glu Cys Ala Pro Thr Ser Asn Pro Asn Asn Thr Phe
290                 295                 300

Val Ala Glu Ser Gln Lys Asn Val Trp Arg Glu Ala Tyr Lys Asn Asp
305                 310                 315                 320

Pro Leu Asn His Ser Lys Met Leu Glu Ile Met Asn Leu Asn Leu Thr
                325                 330                 335

Thr Asn Val Gly Thr Phe Ser Leu Ile Phe Asn Cys Phe Ser Ala Thr
            340                 345                 350

Phe His Val Gly His Arg Val Asp Asn Ala Gln Asp Ala Ile Thr Glu
            355                 360                 365

Gln Val Ser Val Lys Tyr Thr Ser Asp Val Asp Lys Glu Met Tyr Asp
            370                 375                 380

Thr Tyr Tyr Tyr Lys Leu Lys Gln Met Leu Lys Asp Glu Ile Ile Gln
385                 390                 395                 400

Tyr Val Glu Glu His Ile Ala Lys Asn Tyr Arg Asp Val Thr Ala Glu
                405                 410                 415

Ser Leu Ser Ala Leu Ala Asn Ser Ser Asn Gly Phe Ile Lys Glu Val
            420                 425                 430

Glu Phe Val Asp Arg Lys Ile Lys Thr Thr Lys Lys Ile Leu His Leu
            435                 440                 445

Asp Ser Asp Leu Ile Ser Asn Thr Tyr Ser Asp Leu Thr Lys Ser Leu
450                 455                 460

Ser His Gly Ile Pro Met Gly Thr Arg Asn Val Pro Ala Arg Gln Thr
465                 470                 475                 480

Arg Gly Ile Phe Ile Leu Pro Trp Gln Val Ala Ile Gln His Thr
                485                 490                 495

Ile Ala Glu Ser Leu Tyr Lys Arg Ala Lys Lys Gly Ala Tyr Gly Gly
            500                 505                 510

Ser Phe Ala Glu Ala Tyr Thr Ala Lys Thr Ala Ser Leu Thr Tyr Gly
            515                 520                 525

Val Leu Ala Glu Asp Thr Ser Lys Ala Met Arg Ile Ile Leu Tyr Thr
            530                 535                 540

Asp Val Ser Gln Trp Asp Ala Ser Gln His Asn Thr Val Pro Tyr Arg
545                 550                 555                 560

Ser Ala Trp Ile Asn Ala Ile Arg Glu Ala Arg Ser Glu Leu Arg Trp
                565                 570                 575

Asn Tyr Ser Asp Glu Pro Tyr Val Leu Gly Met Asn Val Leu Asp Asn
            580                 585                 590

Met Val Lys Ile Gln Glu Tyr Leu Leu Asn Ser Asn Leu Val Val Ser
            595                 600                 605

Ser Pro Gly Ser Leu Arg Pro Thr Lys Ile Ile Arg Tyr His Gly Val
            610                 615                 620

Ala Ser Gly Glu Lys Thr Thr Lys Ile Gly Asn Ser Phe Ala Asn Val
625                 630                 635                 640

Ala Leu Ile Glu Thr Val Leu Asp Tyr Thr Lys Gln Gln Ile Pro Asp
                645                 650                 655

Leu Glu Ile Ser His Leu Arg Val Asp Gly Asp Asp Asn Val Val Thr
            660                 665                 670
```

```
Ile Asn Thr Ser Cys Pro Ile Glu Arg Leu Gln Ala Ile Lys Asn
            675                 680                 685
Asn Tyr Ser Lys Leu Asn Ala Arg Val Lys Ala Leu Ala Ser Tyr Thr
        690                 695                 700
Gly Leu Glu Met Ala Lys Arg Phe Val Val Cys Gly Lys Ile Phe Glu
705                 710                 715                 720
Arg Gly Ala Ile Pro Ile Phe Thr Ala Glu Arg Pro Tyr Gly Thr Asp
                725                 730                 735
Leu Ser Thr Gln Ser Met Cys Gly Ser Ser Ile Tyr Ser Thr Ala Val
            740                 745                 750
Asn Ala Tyr Arg Gly Phe Gly Asp Glu Tyr Phe Ser Phe Met Leu Asp
        755                 760                 765
Val Leu Val Pro Pro Ser Ser Ser Val Arg Val Thr Gly Arg Leu Arg
    770                 775                 780
Val Leu Leu Ser Pro Val Thr Leu Tyr Ala Thr Gly Pro Leu Ser Phe
785                 790                 795                 800
Glu Val Thr Pro Gln Gly Leu Gly Gly Arg Gly Arg Met Phe Thr Glu
                805                 810                 815
Ser Lys Lys Leu Phe Thr Leu Phe Lys Leu Leu Thr Gln Thr Val Ser
            820                 825                 830
Val Ser Val Thr Pro Glu Asp Ile Lys Lys Tyr Ser Ala Thr Lys Gln
        835                 840                 845
Phe Asn Ala Arg Thr Asp Val Met Ile Lys Ser Met Arg Glu Arg Val
    850                 855                 860
Gly Gly Asp Ala Lys Ala Leu Asn Arg Ile Met Ile Asp Lys Glu Glu
865                 870                 875                 880
Gln Lys Thr Leu Gly Val Pro Asn Val Leu Ser Gln Lys Asn Arg Asp
                885                 890                 895
Gln Val Ser Gln Ala Ile Lys Ile Leu Gly Val Pro Glu Arg Asp Asp
            900                 905                 910
Leu Ser Thr Ser Gly Tyr Tyr Pro Glu Glu Leu Tyr Ser Leu Val Ile
        915                 920                 925
Gln His Ser Val Val Lys Tyr Met Asp Tyr Gly Val Gln His Ser Ile
    930                 935                 940
Tyr Asn Val Asn Cys Glu Pro Val Lys Leu Leu His Ala Gln Leu Gly
945                 950                 955                 960
Ile Arg Ile Ser Asp Ser Lys Pro Ile Ala Lys Pro Val Asn His Leu
                965                 970                 975
Tyr Asp Ile Val Ser Ser Ile Ser Pro Ile Arg Ile Ser Pro Ser Asp
            980                 985                 990
Leu Ile Lys Gln Ala Arg Glu Tyr Asn Leu Thr Ser Tyr Lys Gly Lys
        995                 1000                1005
Arg Glu Phe Leu Leu Asp Leu Gly Leu Asn Gly Asn Thr Leu Lys Thr
    1010                1015                1020
Tyr Leu Ala Ser Lys Leu Leu Phe Arg Asp Leu Met Leu Ser Lys Tyr
1025                1030                1035                1040
Asp Glu Leu Tyr Ser Thr Pro Gly Phe Gly Ala Thr Gln Leu Thr Thr
                1045                1050                1055
Ile Pro Leu Asp Ile Ser Ser Ala Glu Lys Ile Phe Ser Leu Thr Leu
            1060                1065                1070
Lys Leu Pro Ala His Leu Tyr Glu Val Met Leu Leu Leu Tyr
        1075                1080                1085
Glu Tyr Val His Phe Val Phe Ala Cys Lys Arg Thr Phe Thr Ala Thr
```

-continued

```
          1090              1095              1100

Leu His Ile Thr Ser Gln Asp Asp Ala Ala Lys Leu Thr Lys Gln Ile
1105                1110              1115              1120

Leu Gln Met Leu Asp Asp Ile Lys Leu Asp Lys Val Ser Phe Lys Asp
                1125              1130              1135

Glu Ala Trp

<210> SEQ ID NO 5
<211> LENGTH: 2817
<212> TYPE: DNA
<213> ORGANISM: Unknown
<220> FEATURE:
<223> OTHER INFORMATION: Description of Unknown:
      Reoviridae family sequence

<400> SEQUENCE: 5
attttcatga tggattcaca gaatctaata aattctgcga agaccaacat tcaaagtgta      60
gattcaaagg aagaaaaaca aaaaatcttt gaccaattaa cttctgatat tagaagtcag     120
aacgatggga atattccaga tgaggtgatt gctgaattgc aacaactagc agagatcaat     180
ggtttaaaat tttcgtttaa gaaagaagga acaacgctg atagtaga accacctgat       240 ccaacttcag tcttatctca agaggtattt caaattagga cgattctatc caaaactttg     300
tttgttgatg tggaactgga agattattcc gtgtacgtac aacagaaat taaccactta     360 accccgtcc taatagatac gaagccgtta cagacatatc aagttaaagc actaatgtac     420
agagacaccg ccatcatacc atcaactaga tgatgtttt cagatcaata cggagcggat      480
gacattttat ttgattcaca tatgtttaat gatataaatc aagctcaaat tcgcgacttc     540
gatacgtaca tccttgacaa agcggtcgca attagatcca cactacctaa tctaaatttt     600
gtctccgcat tggagaaaga agttaaccct ttcaatgtgc ataacacttt atgtcttgac     660
ttcggtcaac gtgattatta taaccttata tctgatagaa ccaacctttc atttcagcaa     720
agaagacaaa gcatacaatt tgacaacgtt gtcgtggacg gcgttgctcg tacggctaga     780
gtctctctcc gtttgcatcc acttgacagt cagctcctag atattgtaag attcaataca     840
atcgcggatc aacccttggc taatacacta gctgaatatc aactgattgc cgctgacgga     900
tttgttgcta ctccaaaatt tagatttgac agagatatgc gtcttatagc agatgtacgg     960
tcattagtta tggctagact gtgtgaatta tcaccatact ttcatcgaac caggattcta    1020
tcttcaatga tggattttaa tcccctctgg aaaaccaacg ttttttcaag ttcaattgat    1080
aatgctaaag acgccatata cagaatggca gaaatttcat ttactgtgtc agatgcgaca    1140
acatcagctc tttcgactgt aaatgtagca tcagcacaac agaccttaat agtcttatta    1200
aatctttcac ttttcaggtt tgatatagat ccaataggca gtcaatctaa cttcggtgca    1260
gcagtttcag ctgcattgat gttagttatt ttcccaacaa atgaagaagc tatgtctaat    1320
gttacattcg acaatctatg caacttggtg ttcaatgaat taattgcatg gacagttgag    1380
agaccaactt ttgtgaaaag agcaggcgyt acgaacgcgt tcgaagccaa tgtcaatatt    1440
ggaggaggca acatgtctag agacatagtg gcctacatgc gctatgttct cttacgtaga    1500
ccgtgggctg tgtttcagag gtcttatgat gatggatatg tcgcagacat tatgatccca    1560
aacatagatg aggttaatgt caatgaccaa gcctatctag cgattaacaa tcttttcaat    1620
ggactgattc aatcggctca acgcaatcca atcctggca ggcagattgc cgcaacatca     1680
tttagaaagc ttctgaaatc gatgaaagat tcatgttgca acagaattat gccattaatc    1740
```

-continued

```
agattaatga gatacaacat tgaaagagta gctagagtgt ttaggcattt tccatacacg    1800
gcagacctcg tgaatagaat accagctttc cgtgatgaaa gattacgagt taaagtgcca    1860
atttctggag tgttatctat aatgttggga ataaacaagg caccagattt ttttgactgg    1920
tataatctgt taaaatttgc tgacgttgta agggcaaaga actttgctga gagagaatct    1980
ttagaatcaa taatggccca agctgtaatt agaaatgcaa taaatccagc acgttcaaaa    2040
aaagattaca tacaacaaaa cgtcaagccg gccactgccg ttgtagcgtc gctcttgaag    2100
ataccttcag ctacgttcac caccattctc tccgatagga tgttgaataa cgaaatccga    2160
cgtactcaaa gttttgacgt cataaaccgc ataatggatg ccgttcgcgc agcatttgaa    2220
catgtcccaa cagccgaaca tgggattgca aagggcgctt tacttctacc ttatccacag    2280
aattttcaga gatcatccgt atacgttagg aaagataaca tcatttacaa ccctccagtt    2340
ggaatagata gattcgccct tcacgatcta ctggacggtc gattctatca aggaatggtt    2400
aatagaattc agaatatggc gccttttgtg atagttggac cattacagac aaaatccgcc    2460
gatggatctg ctattgattc tgttacgtct gcgtacttaa ctatgtcatc tccatatgat    2520
gcatgcataa gaccagaaga tttacggcat aataaaatag tacagccgcc agtagttgat    2580
tatttcagtg attcaagtat tactagacca atacacaat tgaacagtt gatgtcaaaa     2640 acatcagtat tcattatcga cgccccaaaa ttgatagtgc aaagcgatgc aacggcatac    2700
acgtttgatt ataaagacat tcaattgtcc acatcagtta cggacaaact ggaatttaca    2760
tcagtgcaac caccagatgt cactttattt aatggaatgt tggtctttga ggattag       2817
```

<210> SEQ ID NO 6
<211> LENGTH: 936
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP2
<220> FEATURE:
<221> NAME/KEY: MOD_RES
<222> LOCATION: (468)..(468)
<223> OTHER INFORMATION: Any amino acid

<400> SEQUENCE: 6

```
Met Met Asp Ser Gln Asn Leu Ile Asn Ser Ala Lys Thr Asn Ile Gln
1               5                   10                  15

Ser Val Asp Ser Lys Glu Glu Lys Gln Lys Ile Phe Asp Gln Leu Thr
            20                  25                  30

Ser Asp Ile Arg Ser Gln Asn Asp Gly Asn Ile Pro Asp Glu Val Ile
        35                  40                  45

Ala Glu Leu Gln Gln Leu Ala Glu Ile Asn Gly Leu Lys Phe Ser Phe
    50                  55                  60

Lys Lys Glu Gly Asn Asn Ala Glu Ile Val Glu Pro Pro Asp Pro Thr
65                  70                  75                  80

Ser Val Leu Ser Gln Glu Val Phe Gln Ile Arg Thr Ile Leu Ser Lys
                85                  90                  95

Thr Leu Phe Val Asp Val Glu Leu Glu Asp Tyr Ser Val Tyr Val Pro
            100                 105                 110

Thr Glu Ile Asn His Leu Thr Pro Val Leu Ile Asp Thr Lys Pro Leu
        115                 120                 125

Gln Thr Tyr Gln Val Lys Ala Leu Met Tyr Arg Asp Thr Ala Ile Ile
    130                 135                 140
```

```
Pro Ser Thr Arg Asp Asp Val Ser Asp Gln Tyr Gly Ala Asp Asp Ile
145                 150                 155                 160

Leu Phe Asp Ser His Met Phe Asn Asp Ile Asn Gln Ala Gln Ile Arg
                165                 170                 175

Asp Phe Asp Thr Tyr Ile Leu Asp Lys Ala Val Ala Ile Arg Ser Thr
            180                 185                 190

Leu Pro Asn Leu Asn Phe Val Ser Ala Leu Glu Lys Glu Val Asn Pro
                195                 200                 205

Phe Asn Val His Asn Thr Leu Cys Leu Asp Phe Gly Gln Arg Asp Tyr
        210                 215                 220

Tyr Asn Leu Ile Ser Asp Arg Thr Asn Leu Ser Phe Gln Gln Arg Arg
225                 230                 235                 240

Gln Ser Ile Gln Phe Asp Asn Val Val Asp Gly Val Ala Arg Thr
                245                 250                 255

Ala Arg Val Ser Leu Arg Leu His Pro Leu Asp Ser Gln Leu Leu Asp
                260                 265                 270

Ile Val Arg Phe Asn Thr Ile Ala Asp Gln Pro Leu Ala Asn Thr Leu
            275                 280                 285

Ala Glu Tyr Gln Leu Ile Ala Ala Asp Gly Phe Val Ala Thr Pro Lys
            290                 295                 300

Phe Arg Phe Asp Arg Asp Met Arg Leu Ile Ala Asp Val Arg Ser Leu
305                 310                 315                 320

Val Met Ala Arg Leu Cys Glu Leu Ser Pro Tyr Phe His Arg Thr Arg
                325                 330                 335

Ile Leu Ser Ser Met Met Asp Phe Asn Pro Leu Trp Lys Thr Asn Val
                340                 345                 350

Phe Ser Ser Ser Ile Asp Asn Ala Lys Asp Ala Ile Tyr Arg Met Ala
            355                 360                 365

Glu Ile Ser Phe Thr Val Ser Asp Ala Thr Thr Ser Ala Leu Ser Thr
        370                 375                 380

Val Asn Val Ala Ser Ala Gln Gln Thr Leu Ile Val Leu Leu Asn Leu
385                 390                 395                 400

Ser Leu Phe Arg Phe Asp Ile Asp Pro Ile Gly Ser Gln Ser Asn Phe
                405                 410                 415

Gly Ala Ala Val Ser Ala Ala Leu Met Leu Val Ile Phe Pro Thr Asn
            420                 425                 430

Glu Glu Ala Met Ser Asn Val Thr Phe Asp Asn Leu Cys Asn Leu Val
        435                 440                 445

Phe Asn Glu Leu Ile Ala Trp Thr Val Glu Arg Pro Thr Phe Val Lys
450                 455                 460

Arg Ala Gly Xaa Thr Asn Ala Phe Glu Ala Asn Val Asn Ile Gly Gly
465                 470                 475                 480

Gly Asn Met Ser Arg Asp Ile Val Ala Tyr Met Arg Tyr Val Leu Leu
                485                 490                 495

Arg Arg Pro Trp Ala Val Phe Gln Arg Ser Tyr Asp Asp Gly Tyr Val
            500                 505                 510

Ala Asp Ile Met Ile Pro Asn Ile Asp Glu Val Asn Val Asn Asp Gln
            515                 520                 525

Ala Tyr Leu Ala Ile Asn Asn Leu Phe Asn Gly Leu Ile Gln Ser Ala
        530                 535                 540

Gln Arg Asn Pro Asn Pro Gly Arg Gln Ile Ala Ala Thr Ser Phe Arg
545                 550                 555                 560
```

```
Lys Leu Leu Lys Ser Met Lys Asp Ser Cys Cys Asn Arg Ile Met Pro
                565                 570                 575

Leu Ile Arg Leu Met Arg Tyr Asn Ile Glu Arg Val Ala Arg Val Phe
            580                 585                 590

Arg His Phe Pro Tyr Thr Ala Asp Leu Val Asn Arg Ile Pro Ala Phe
        595                 600                 605

Arg Asp Glu Arg Leu Arg Val Lys Val Pro Ile Ser Gly Val Leu Ser
    610                 615                 620

Ile Met Leu Gly Ile Asn Lys Ala Pro Asp Phe Phe Asp Trp Tyr Asn
625                 630                 635                 640

Leu Leu Lys Phe Ala Asp Val Val Arg Ala Lys Asn Phe Ala Glu Arg
                645                 650                 655

Glu Ser Leu Glu Ser Ile Met Ala Gln Ala Val Ile Arg Asn Ala Ile
            660                 665                 670

Asn Pro Ala Arg Ser Lys Lys Asp Tyr Ile Gln Gln Asn Val Lys Pro
        675                 680                 685

Ala Thr Ala Val Val Ala Ser Leu Leu Lys Ile Pro Ser Ala Thr Phe
    690                 695                 700

Thr Thr Ile Leu Ser Asp Arg Met Leu Asn Asn Glu Ile Arg Arg Thr
705                 710                 715                 720

Gln Ser Phe Asp Val Ile Asn Arg Ile Met Asp Ala Val Arg Ala Ala
                725                 730                 735

Phe Glu His Val Pro Thr Ala Glu His Gly Ile Ala Lys Gly Ala Leu
            740                 745                 750

Leu Leu Pro Tyr Pro Gln Asn Phe Gln Arg Ser Ser Tyr Val Arg
        755                 760                 765

Lys Asp Asn Ile Ile Tyr Asn Pro Pro Val Gly Ile Asp Arg Phe Ala
    770                 775                 780

Leu His Asp Leu Leu Asp Gly Arg Phe Tyr Gln Gly Met Val Asn Arg
785                 790                 795                 800

Ile Gln Asn Met Ala Pro Phe Val Ile Val Gly Pro Leu Gln Thr Lys
                805                 810                 815

Ser Ala Asp Gly Ser Ala Ile Asp Ser Val Thr Ser Ala Tyr Leu Thr
            820                 825                 830

Met Ser Ser Pro Tyr Asp Ala Cys Ile Arg Pro Glu Asp Leu Arg His
        835                 840                 845

Asn Lys Ile Val Gln Pro Pro Val Val Asp Tyr Phe Ser Asp Ser Ser
    850                 855                 860

Ile Thr Arg Pro Asn Thr Gln Phe Glu Gln Leu Met Ser Lys Thr Ser
865                 870                 875                 880

Val Phe Ile Ile Asp Ala Pro Lys Leu Ile Val Gln Ser Asp Ala Thr
                885                 890                 895

Ala Tyr Thr Phe Asp Tyr Lys Asp Ile Gln Leu Ser Thr Ser Val Thr
            900                 905                 910

Asp Lys Leu Glu Phe Thr Ser Val Gln Pro Pro Asp Val Thr Leu Phe
        915                 920                 925

Asn Gly Met Leu Val Phe Glu Asp
    930                 935

<210> SEQ ID NO 7
<211> LENGTH: 2339
<212> TYPE: DNA
<213> ORGANISM: Unknown
<220> FEATURE:
<223> OTHER INFORMATION: Description of Unknown:
```

-continued

Reoviridae family sequence

<400> SEQUENCE: 7

```
acattatgtc aaagctcatt gagttttcag atctgggtgc tgagatctca aatagagagg     60
aactttttaa actttcaaat aacgtgtcat cttttgaggt aatcaaacca acaaagaaca    120
ttgaggatta tattcgagac agtacacatt atgtaatagt cgataggagg ctaaataatg    180
aagtttctga catacttgat acactgtttc ctacttcagt tatttttaac agtgaggaag    240
gctataagtt tggtggttgt agacatcttc ttgacaatgt tcttcatgtt agccaccata    300
tgtacagcta tcttaacggg agcgatcaaa gttggctacc tactgggtgg tctgttagtg    360
aatgcgatgg atttgatgat catattggag accagataat taagcacata gtaaatacat    420
gttcaataca gacagaggga caaatgaaaa atctaaaacc aggtacttat ccaaaattag    480
agagagttaa tgaagctttc aaaggttttt taactaagat tactgtacct caaaccagta    540
tggattttca gtcttataac tatatggtgc agcgcaaaca aattggttat gtggtaagaa    600
aaacagtgtt tcatcttata agaaaacata actggaatgt taattacgtg ggtcctgaat    660
ttgaatcttt taaagacatc attctactat taactgatcg caactatact ggtaaattca    720
ttacatacac actaaacact gctaagaaac acaactatag agcaaaagag agagaaaaca    780
attctaaaaa agcaggatgg gactttgtac ataggctcag acataaattt gaaaatgcat    840
tttgtcatct aatgtacaat catgttgcaa aacaacgtag ctactcaaca atttatgtta    900
acaagttgta taacgttgga aactgggtgg gggcatattc atggttgaac ataaacttag    960
ttgatcactt accaaccatt cagaaaaact cagtcgtgtt tggatttctg ttatcatcta   1020
aggattgttc attttccgtc aatactctat cggacattgt ggtgtactca ccacaaccat   1080
atgatgatga ctctaattac tggactgtat caataatggg agaatttata ggacatttag   1140
caaatgaaga gtctagaata gcggaaaaaa acaacaactt accaaactat gtatttggcg   1200
gtgtcccatt tacagctgag gcattggatc ttaatcgaat tacaatagca ctttactcat   1260
tgtccaatgc ctttaattca cctgaactca tcaaagcaac cttatcatat aatcatatat   1320
ttacctttcc aacgtactca gacggtaatt ggagagatga gagaccagtg catgacaaga   1380
tattcgttac gactcagaaa caactaaggt ttgaagattg gattattgac gtaaagaact   1440
tgtcattgga gatgaacata gaggtggttg cagagagtgt tttcctacaa tttggacctc   1500
atagggcgtt cataacggat atgtttcaac atatggtttc attcagattc aagcaagaga   1560
atttttttc tgatcagaaa atgtcgcact ttggaatccg tcagccttca atacataaca   1620
gagataagta tctttcatct aggctgaacg cctatatcaa tagacaacta acactaggta   1680
cagatttaac tgtgattaga aaaaacaact tcgcaggatt ttctgggcac ttaatagcgg   1740
tcgaaaaata ctttcatgca ctagtctaca ccatgtctcc gatgagatgg gctaccagag   1800
ctctttcaga cgctacttac aaaaaacatg acaatttttc taatgctatt ggggaaaggc   1860
atacattgga tgattttcgt aatacatatg cgtatcttgg tagttccgtt aatccaatac   1920
taaggtacaa acttgtcaac gataaatatg ctgatgagcc aaaatacgca attatgttaa   1980
tgtgtggaaa taatcatatc actttacaac taactacaaa agatccatca aatctcttaa   2040
ctgaaattgg taatataata catggtttga atatcaagta tttaggtaag aactcgtttg   2100
gtaatatcaa actggcccta taccagacta aagatatgtt acaatataaa ctaagcaact   2160
tgctgagatc gtttgacata ccttgtcagc agcatagacc atacataatg cacatgacct   2220
tgaaagatgg cagcaacgta ccagatgtaa taatagcaca cagaagagat attaagatca   2280
```
aagaaattaa gcactgagct gacatactag accagagtgg tcggatacac ataaaaacc    2339

<210> SEQ ID NO 8
<211> LENGTH: 763
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP3

<400> SEQUENCE: 8

Met Ser Lys Leu Ile Glu Phe Ser Asp Leu Gly Ala Glu Ile Ser Asn
1               5                   10                  15

Arg Glu Glu Leu Phe Lys Leu Ser Asn Asn Val Ser Ser Phe Glu Val
            20                  25                  30

Ile Lys Pro Thr Lys Asn Ile Glu Asp Tyr Ile Arg Asp Ser Thr His
        35                  40                  45

Tyr Val Ile Val Asp Arg Arg Leu Asn Asn Glu Val Ser Asp Ile Leu
    50                  55                  60

Asp Thr Leu Phe Pro Thr Ser Val Ile Phe Asn Ser Glu Glu Gly Tyr
65                  70                  75                  80

Lys Phe Gly Gly Cys Arg His Leu Leu Asp Asn Val Leu His Val Ser
                85                  90                  95

His His Met Tyr Ser Tyr Leu Asn Gly Ser Asp Gln Ser Trp Leu Pro
            100                 105                 110

Thr Gly Trp Ser Val Ser Glu Cys Asp Gly Phe Asp Asp His Ile Gly
        115                 120                 125

Asp Gln Ile Ile Lys His Ile Val Asn Thr Cys Ser Ile Gln Thr Glu
    130                 135                 140

Gly Gln Met Lys Asn Leu Lys Pro Gly Thr Tyr Pro Lys Leu Glu Arg
145                 150                 155                 160

Val Asn Glu Ala Phe Lys Gly Phe Leu Thr Lys Ile Thr Val Pro Gln
                165                 170                 175

Thr Ser Met Asp Phe Gln Ser Tyr Asn Tyr Met Val Gln Arg Lys Gln
            180                 185                 190

Ile Gly Tyr Val Val Arg Lys Thr Val Phe His Leu Ile Arg Lys His
        195                 200                 205

Asn Trp Asn Val Asn Tyr Val Gly Pro Glu Phe Glu Ser Phe Lys Asp
    210                 215                 220

Ile Ile Leu Leu Leu Thr Asp Arg Asn Tyr Thr Gly Lys Phe Ile Thr
225                 230                 235                 240

Tyr Thr Leu Asn Thr Ala Lys Lys His Asn Tyr Arg Ala Lys Glu Arg
                245                 250                 255

Glu Asn Asn Ser Lys Lys Ala Gly Trp Asp Phe Val His Arg Leu Arg
            260                 265                 270

His Lys Phe Glu Asn Ala Phe Cys His Leu Met Tyr Asn His Val Ala
        275                 280                 285

Lys Gln Arg Ser Tyr Ser Thr Ile Tyr Val Asn Lys Leu Tyr Asn Val
    290                 295                 300

Gly Asn Trp Val Gly Ala Tyr Ser Trp Leu Asn Ile Asn Leu Val Asp
305                 310                 315                 320

His Leu Pro Thr Ile Gln Lys Asn Ser Val Val Phe Gly Phe Leu Leu
                325                 330                 335

-continued

```
Ser Ser Lys Asp Cys Ser Phe Ser Val Asn Thr Leu Ser Asp Ile Val
            340                 345                 350
Val Tyr Ser Pro Gln Pro Tyr Asp Asp Ser Asn Tyr Trp Thr Val
        355                 360                 365
Ser Ile Met Gly Glu Phe Ile Gly His Leu Ala Asn Glu Glu Ser Arg
370                 375                 380
Ile Ala Glu Lys Asn Asn Asn Leu Pro Asn Tyr Val Phe Gly Gly Val
385                 390                 395                 400
Pro Phe Thr Ala Glu Ala Leu Asp Leu Asn Arg Ile Thr Ile Ala Leu
                405                 410                 415
Tyr Ser Leu Ser Asn Ala Phe Asn Ser Pro Glu Leu Ile Lys Ala Thr
        420                 425                 430
Leu Ser Tyr Asn His Ile Phe Thr Phe Pro Thr Tyr Ser Asp Gly Asn
        435                 440                 445
Trp Arg Asp Glu Arg Pro Val His Asp Lys Ile Phe Val Thr Thr Gln
    450                 455                 460
Lys Gln Leu Arg Phe Glu Asp Trp Ile Ile Asp Val Lys Asn Leu Ser
465                 470                 475                 480
Leu Glu Met Asn Ile Glu Val Val Ala Glu Ser Val Phe Leu Gln Phe
                485                 490                 495
Gly Pro His Arg Ala Phe Ile Thr Asp Met Phe Gln His Met Val Ser
            500                 505                 510
Phe Arg Phe Lys Gln Glu Asn Phe Ser Asp Gln Lys Met Ser His
        515                 520                 525
Phe Gly Ile Arg Gln Pro Ser Ile His Asn Arg Asp Lys Tyr Leu Ser
    530                 535                 540
Ser Arg Leu Asn Ala Tyr Ile Asn Arg Gln Leu Thr Leu Gly Thr Asp
545                 550                 555                 560
Leu Thr Val Ile Arg Lys Asn Asn Phe Ala Gly Phe Ser Gly His Leu
                565                 570                 575
Ile Ala Val Glu Lys Tyr Phe His Ala Leu Val Tyr Thr Met Ser Pro
            580                 585                 590
Met Arg Trp Ala Thr Arg Ala Leu Ser Asp Ala Thr Tyr Lys Lys His
        595                 600                 605
Asp Asn Phe Ser Asn Ala Ile Gly Glu Arg His Thr Leu Asp Asp Phe
    610                 615                 620
Arg Asn Thr Tyr Ala Tyr Leu Gly Ser Ser Val Asn Pro Ile Leu Arg
625                 630                 635                 640
Tyr Lys Leu Val Asn Asp Lys Tyr Ala Asp Glu Pro Lys Tyr Ala Ile
                645                 650                 655
Met Leu Met Cys Gly Asn Asn His Ile Thr Leu Gln Leu Thr Thr Lys
            660                 665                 670
Asp Pro Ser Asn Leu Leu Thr Glu Ile Gly Asn Ile Ile His Gly Leu
        675                 680                 685
Asn Ile Lys Tyr Leu Gly Lys Asn Ser Phe Gly Asn Ile Lys Leu Ala
        690                 695                 700
Leu Tyr Gln Thr Lys Asp Met Leu Gln Tyr Lys Leu Ser Asn Leu Leu
705                 710                 715                 720
Arg Ser Phe Asp Ile Pro Cys Gln Gln His Arg Pro Tyr Ile Met His
                725                 730                 735
Met Thr Leu Lys Asp Gly Ser Asn Val Pro Asp Val Ile Ile Ala His
            740                 745                 750
Arg Arg Asp Ile Lys Ile Lys Glu Ile Lys His
```

<210> SEQ ID NO 9
<211> LENGTH: 2287
<212> TYPE: DNA
<213> ORGANISM: Unknown
<220> FEATURE:
<223> OTHER INFORMATION: Description of Unknown:
      Reoviridae family sequence

<400> SEQUENCE: 9

| | | | | | |
|---|---|---|---|---|---|
| ccaggatgct | ttcttatcta | agacgagaat | ggcagtctta | tggggagagt | gccacgaacg | 60 |
| ttaaagagga | ggaagacaca | acgaatgaca | atggaaaagg | aaataaagtt | gagaaaccag | 120 |
| ttaaagctga | aaacaggtat | tgttacagaa | gtccacaaga | aaagataaa | tatgaatcag | 180 |
| atcttcaagg | cttttcactg | ggaacgcaag | atgaacatat | aaacccaacg | acattacaga | 240 |
| tatacgatgg | aatattgagc | aatggacata | cgttcataaa | cacagaccca | ccttgctcga | 300 |
| caatcttcga | attgaatatc | atggcagaga | gtggagcaat | ggttgataac | aaaccactga | 360 |
| tggatttcaa | ttgttttata | acatcaataa | agaaagatga | aaacggggta | tgtgatataa | 420 |
| cttatcactg | catgtcagac | ttggatgacg | cgcagaaaag | aatactacta | agaggattct | 480 |
| ccagtaaagg | ttgttcagga | ttgaatgata | tgaaagttac | ttctatactt | cgcatagtgg | 540 |
| ataaagcttt | agggtctgaa | tttcatacaa | gaactcaagc | atcgttatat | acgtgggata | 600 |
| gtgactgcat | cgaaagctat | gatggtaaaa | tcagagttgg | tgaaagaaaa | gtaggcaact | 660 |
| cgcgtataat | aatttacgag | caagaagatg | gtttctggaa | aatattgacc | gaaacacttt | 720 |
| ggattgattt | gagagctgta | tttaaaccat | atggaattat | gggtggtgct | tttaaaaatt | 780 |
| ggctggtaga | ttctggattc | gacaaatatg | aataccagta | cagctacgaa | cgggaaggta | 840 |
| aaacggtttc | ggcaaccacc | attacgtatc | caaaaccaac | aggaaaagcc | ggcgtgaacc | 900 |
| agccatggag | accggcaaca | gattacaatg | gtcagtatgt | gtgtttacag | ccaggggata | 960 |
| ctttcacggt | atggtatttt | gaagaccagt | ggcagattcg | caatgcgata | tatgcaaaaa | 1020 |
| atttccaatc | cgacactatg | gcaagggag | tactggaaaa | caaggtcca | ctaatttta | 1080 |
| agatgaacta | tattccaagt | ctagccagta | taaaaaataa | gccgggaaaa | gtgcaataca | 1140 |
| gatatatgaa | tggtggtttc | gcgcaagttg | acgcaagttc | atatactggt | atggcactga | 1200 |
| ttttcaattt | cgagtgtgtt | ggtaaaaaat | tttacactga | agactataaa | acgaaaattg | 1260 |
| acaattcaat | tacaccatat | atatgtttta | ttggaaaaaa | ctacacacct | gacgggtatt | 1320 |
| tttatgaaaa | aggatgttgt | tcagggtttg | ctgcaggata | tgatacagaa | acgatttcac | 1380 |
| acaaaatgac | aatatcatat | acggtgatgc | gcccttcaga | tccggagttc | gtaactggag | 1440 |
| gtgatgcata | tggacaaagt | atcacatcaa | acctagaagt | atctatacga | gatcttcaag | 1500 |
| atcaaataaa | ctcaatacgt | gcagaactga | atatttcgca | agtaacgtcg | gcagtatttt | 1560 |
| ctgctatcac | atctttaggt | gatttaccga | gtttattctc | gaacataaca | caaatataca | 1620 |
| gtaaactgaa | agacgctctt | ttaaagctta | aaactagaaa | gagtaaacca | aaacctatta | 1680 |
| aagcaactat | gatagtggat | agaaacacgt | tagatgtacc | aaatgtcagt | atactaaata | 1740 |
| gaatgccaga | agaattagaa | gtaggtatca | tctacaattc | tataaggaaa | ccagaaaaac | 1800 |
| acgatattcc | taaattcgcc | ttgtctacag | aattggaact | accttacatc | caaactacat | 1860 |
| ccactataac | tccaaaattt | agaaaatatt | tagaagaaag | agggctgcta | acgatagatg | 1920 |
| atatagcggt | acaatttgac | cctttagatg | tgacatttc | aacacttagg | agaaaaaatg | 1980 |

```
ctgaaatcat gaaatataag attgacccgg aaatagcgya tgaagttctg tctcaaatgt    2040
ctaactcagc aactagatca ttgttttctc taaatgttag gaagcaaata tcaacacata    2100
atgagttttc aacaccaaca tatgaacagc taataaatcg tattttgaat gataaagaaa    2160
tattagatgt gttgggaaaa ctgaaccctc aatcagttgg caacatgttc caagagttcg    2220
ttaacagaat gcaaaatatg ttgtcttact attgagcatc ctgaagcacg tatatatttt    2280
aaaaacc                                                              2287
```

```
<210> SEQ ID NO 10
<211> LENGTH: 749
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP4
<220> FEATURE:
<221> NAME/KEY: MOD_RES
<222> LOCATION: (672)..(672)
<223> OTHER INFORMATION: Any amino acid

<400> SEQUENCE: 10

Met Leu Ser Tyr Leu Arg Arg Glu Trp Gln Ser Tyr Gly Glu Ser Ala
1               5                   10                  15

Thr Asn Val Lys Glu Glu Glu Asp Thr Thr Asn Asp Asn Gly Lys Gly
            20                  25                  30

Asn Lys Val Glu Lys Pro Val Lys Ala Glu Asn Arg Tyr Cys Tyr Arg
        35                  40                  45

Ser Pro Gln Glu Lys Asp Lys Tyr Glu Ser Asp Leu Gln Gly Phe Ser
    50                  55                  60

Leu Gly Thr Gln Asp Glu His Ile Asn Pro Thr Thr Leu Gln Ile Tyr
65                  70                  75                  80

Asp Gly Ile Leu Ser Asn Gly His Thr Phe Ile Asn Thr Asp Pro Pro
                85                  90                  95

Cys Ser Thr Ile Phe Glu Leu Asn Ile Met Ala Glu Ser Gly Ala Met
            100                 105                 110

Val Asp Asn Lys Pro Leu Met Asp Phe Asn Cys Phe Ile Thr Ser Ile
        115                 120                 125

Lys Lys Asp Glu Asn Gly Val Cys Asp Ile Thr Tyr His Cys Met Ser
    130                 135                 140

Asp Leu Asp Asp Ala Gln Lys Arg Ile Leu Leu Arg Gly Phe Ser Ser
145                 150                 155                 160

Lys Gly Cys Ser Gly Leu Asn Asp Met Lys Val Thr Ser Ile Leu Arg
                165                 170                 175

Ile Val Asp Lys Ala Leu Gly Ser Glu Phe His Thr Arg Thr Gln Ala
            180                 185                 190

Ser Leu Tyr Thr Trp Asp Ser Asp Cys Ile Glu Ser Tyr Asp Gly Lys
        195                 200                 205

Ile Arg Val Gly Glu Arg Lys Val Gly Asn Ser Arg Ile Ile Ile Tyr
    210                 215                 220

Glu Gln Glu Asp Gly Phe Trp Lys Ile Leu Thr Glu Thr Leu Trp Ile
225                 230                 235                 240

Asp Leu Arg Ala Val Phe Lys Pro Tyr Gly Ile Met Gly Gly Ala Phe
                245                 250                 255

Lys Asn Trp Leu Val Asp Ser Gly Phe Asp Lys Tyr Glu Tyr Gln Tyr
            260                 265                 270
```

```
Ser Tyr Glu Arg Glu Gly Lys Thr Val Ser Ala Thr Thr Ile Thr Tyr
        275                 280                 285

Pro Lys Pro Thr Gly Lys Ala Gly Val Asn Gln Pro Trp Arg Pro Ala
    290                 295                 300

Thr Asp Tyr Asn Gly Gln Tyr Val Cys Leu Gln Pro Gly Asp Thr Phe
305                 310                 315                 320

Thr Val Trp Tyr Phe Glu Asp Gln Trp Gln Ile Arg Asn Ala Ile Tyr
                325                 330                 335

Ala Lys Asn Phe Gln Ser Asp Thr Met Ala Lys Gly Val Leu Glu Asn
            340                 345                 350

Lys Gly Pro Leu Ile Phe Lys Met Asn Tyr Ile Pro Ser Leu Ala Ser
        355                 360                 365

Ile Lys Asn Lys Pro Gly Lys Val Gln Tyr Arg Tyr Met Asn Gly Gly
    370                 375                 380

Phe Ala Gln Val Asp Ala Ser Ser Tyr Thr Gly Met Ala Leu Ile Phe
385                 390                 395                 400

Asn Phe Glu Cys Val Gly Lys Lys Phe Tyr Thr Glu Asp Tyr Lys Thr
                405                 410                 415

Lys Ile Asp Asn Ser Ile Thr Pro Tyr Ile Cys Phe Ile Gly Lys Asn
            420                 425                 430

Tyr Thr Pro Asp Gly Tyr Phe Tyr Glu Lys Gly Cys Cys Ser Gly Phe
        435                 440                 445

Ala Ala Gly Tyr Asp Thr Glu Thr Ile Ser His Lys Met Thr Ile Ser
    450                 455                 460

Tyr Thr Val Met Arg Pro Ser Asp Pro Glu Phe Val Thr Gly Gly Asp
465                 470                 475                 480

Ala Tyr Gly Gln Ser Ile Thr Ser Asn Leu Glu Val Ser Ile Arg Asp
                485                 490                 495

Leu Gln Asp Gln Ile Asn Ser Ile Arg Ala Glu Leu Asn Ile Ser Gln
            500                 505                 510

Val Thr Ser Ala Val Phe Ser Ala Ile Thr Ser Leu Gly Asp Leu Pro
        515                 520                 525

Ser Leu Phe Ser Asn Ile Thr Gln Ile Tyr Ser Lys Leu Lys Asp Ala
    530                 535                 540

Leu Leu Lys Leu Lys Thr Arg Lys Ser Lys Pro Lys Pro Ile Lys Ala
545                 550                 555                 560

Thr Met Ile Val Asp Arg Asn Thr Leu Asp Val Pro Asn Val Ser Ile
                565                 570                 575

Leu Asn Arg Met Pro Glu Glu Leu Glu Val Gly Ile Ile Tyr Asn Ser
            580                 585                 590

Ile Arg Lys Pro Glu Lys His Asp Ile Pro Lys Phe Ala Leu Ser Thr
        595                 600                 605

Glu Leu Glu Leu Pro Tyr Ile Gln Thr Thr Ser Thr Ile Thr Pro Lys
    610                 615                 620

Phe Arg Lys Tyr Leu Glu Glu Arg Gly Leu Leu Thr Ile Asp Asp Ile
625                 630                 635                 640

Ala Val Gln Phe Asp Pro Leu Asp Val Thr Phe Ser Thr Leu Arg Arg
                645                 650                 655

Lys Asn Ala Glu Ile Met Lys Tyr Lys Ile Asp Pro Glu Ile Ala Xaa
            660                 665                 670

Glu Val Leu Ser Gln Met Ser Asn Ser Ala Thr Arg Ser Leu Phe Ser
        675                 680                 685
```

-continued

```
Leu Asn Val Arg Lys Gln Ile Ser Thr His Asn Glu Phe Ser Thr Pro
        690                 695                 700
Thr Tyr Glu Gln Leu Ile Asn Arg Ile Leu Asn Asp Lys Glu Ile Leu
705                 710                 715                 720
Asp Val Leu Gly Lys Leu Asn Pro Gln Ser Val Gly Asn Met Phe Gln
                725                 730                 735
Glu Phe Val Asn Arg Met Gln Asn Met Leu Ser Tyr Tyr
                740                 745
```

<210> SEQ ID NO 11
<211> LENGTH: 1277
<212> TYPE: DNA
<213> ORGANISM: Unknown
<220> FEATURE:
<223> OTHER INFORMATION: Description of Unknown:
      Reoviridae family sequence

<400> SEQUENCE: 11

```
ggtataatac gggtgtgctg tctgtacaag tcagggaaac ctatgggaaa taggcagtcc    60
agcttgcaat cgcagacgca tcgcactgat attaattctc ataattcaaa cattttcctc   120
cagagtgcat cttccgctga atttagaact cagcatatac taattactgc cggtgctgct   180
ttaatcgcct ttctactcgc tctccttatt tcgagtctag tgtgtaattg ttacctgcta   240
cgaaggttaa gaaatggatc tcgtaaaatt tatcgcacag gcaaagtaca agaaggatct   300
tatcccaatt tatctaaaca attcattcga cccgaccact tgtctaaaa accctttaaa    360
gttagaactc attaagtata caatccatt tcgtgaggtg cctcaactcg caggggaatc    420
tcttttactg gaagatgttt gcccttacaa ccatgagcat ttctgtggcg gcatacacat   480
tccaaagcaa ttcaacatgt caccaaaagg aagaattagt catatcacaa atgcaaaaat   540
tgcatgrcca tgcggtttgg aatctataat tattgatgga agaaatacaa ctggttccgc   600
atttgtcaaa tgtagatgcg ggcaaccata tccaacaatt attgaccaac atcgactttt   660
cttcttccta acttgttgtt caaatgatac gaagtcagtg aaaattggat taagtgaaaa   720
cttcaattgt ttaaattgta acagaagtgt gcgttggttc agtccaggaa gaggactgag   780
gactacgcat caatattacc ttccaagtca gctatgtcca gcatgcatgc catttcgcga   840
tttagtcgct tcaatgtctt tattaaacaa agtggaattt cttggcgctg actttgctca   900
aatgcgcact gattttgagt ggaaaagaca gttgcagaac aactgtgaat ctgcctttag   960
atcattcaac tctccacaat tagcgcatag agttacacca tacgaaagga ttgatccgaa  1020
tctcactctc aacactgtta ctgagaccat ttcctcagtg aacagaagac agcacaacaa  1080
aatagaaatc actccaatat gcagaggaaa gatcgcgatt agcgacggat acagacgatg  1140
cattcttgat tttcaagata atgctgaatt tcactgctca gttaatatgc tattgcttcg  1200
ctggaagctc atctgaacat agaatgagag ttccagatct ctaacctgac gcagccactc  1260
accctatccg aaaaacc                                                 1277
```

<210> SEQ ID NO 12
<211> LENGTH: 320
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: NSP1
<220> FEATURE:
<221> NAME/KEY: MOD_RES
<222> LOCATION: (98)..(98)
<223> OTHER INFORMATION: Any amino acid

<400> SEQUENCE: 12

```
Met Asp Leu Val Lys Phe Ile Ala Gln Ala Lys Tyr Lys Asp Leu
1               5                   10                  15

Ile Pro Ile Tyr Leu Asn Asn Ser Phe Asp Pro Thr Thr Leu Ser Lys
            20                  25                  30

Lys Pro Leu Lys Leu Glu Leu Ile Lys Tyr Asn Asn Pro Phe Arg Glu
        35                  40                  45

Val Pro Gln Leu Ala Gly Glu Ser Leu Leu Glu Asp Val Cys Pro
50                  55                  60

Tyr Asn His Glu His Phe Cys Gly Gly Ile His Ile Pro Lys Gln Phe
65                  70                  75                  80

Asn Met Ser Pro Lys Gly Arg Ile Ser His Ile Thr Asn Asp Lys Ile
                85                  90                  95

Ala Xaa Pro Cys Gly Leu Glu Ser Ile Ile Asp Gly Lys Lys Tyr
            100                 105                 110

Thr Gly Ser Ala Phe Val Lys Cys Arg Cys Gly Gln Pro Tyr Pro Thr
        115                 120                 125

Ile Ile Asp Gln Pro Ser Thr Phe Phe Leu Thr Cys Cys Ser Asn
130                 135                 140

Asp Thr Lys Ser Val Lys Ile Gly Leu Ser Glu Asn Phe Asn Cys Leu
145                 150                 155                 160

Asn Cys Asn Arg Ser Val Arg Trp Phe Ser Pro Gly Arg Gly Leu Arg
                165                 170                 175

Thr Thr His Gln Tyr Tyr Leu Pro Ser Gln Leu Cys Pro Ala Cys Met
            180                 185                 190

Pro Phe Arg Asp Leu Val Ala Ser Met Ser Leu Leu Asn Lys Val Glu
        195                 200                 205

Phe Leu Gly Ala Asp Phe Ala Gln Met Arg Thr Asp Phe Glu Trp Lys
210                 215                 220

Arg Gln Leu Gln Asn Asn Cys Glu Ser Ala Phe Arg Ser Phe Asn Ser
225                 230                 235                 240

Pro Gln Leu Ala His Arg Val Thr Pro Tyr Glu Arg Ile Asp Pro Asn
                245                 250                 255

Leu Thr Leu Asn Thr Val Thr Glu Thr Ile Ser Ser Val Asn Arg Arg
            260                 265                 270

Gln His Asn Lys Ile Glu Ile Thr Pro Ile Cys Arg Gly Lys Ile Ala
        275                 280                 285

Ile Ser Asp Gly Tyr Arg Arg Cys Ile Leu Asp Phe Gln Asp Asn Ala
290                 295                 300

Glu Phe His Cys Ser Val Asn Met Leu Leu Leu Arg Trp Lys Leu Ile
305                 310                 315                 320
```

<210> SEQ ID NO 13
<211> LENGTH: 1259
<212> TYPE: DNA
<213> ORGANISM: Unknown
<220> FEATURE:
<223> OTHER INFORMATION: Description of Unknown:
    Reoviridae family sequence

<400> SEQUENCE: 13

```
ggattaaata acccaactga cgcttcaagc atggatctga ttgaaacagt taatgcatgc    60
gttagattgc aaaaaagaat tctaaactta gctccgaaca cgaatttgaa cacatcaggc   120
```

```
caaagcactc tgaatgacta caatgcattg gcttcaaggt gcaatgggag aacatacgct     180
tttcttgatc aaaccgcagt tcttactcct tttaccatta acgccccaat catttctctc     240
tcggtccgta tatccacaga tgattatgat gacatgaggt ctggaataaa ctcaattta      300 gacgtgctcg ccgctgctat tagaacagaa ggatctagac cagtaagagc aatagaaaga     360
cgtgttcttg aacccgccgt taaacagttg gtagaagacc taaagctgaa aagtctaact     420
tccgaaattt ccgttgcgaa tttagcagct gtagatactg ccataattca accagaaatc     480
attcaaactg agaatccatt atatgccgat gttattgaac aagttgtaaa caggccacaa     540
atgaatatga ctggcggaaa tattagwgct actttaggaa ggtggtcagg caacaaagga     600
gtagttacat gtatgtcagg aatggattcg gaacacagat ttactgttga ccttaaagct     660
aggaccactg gaataatcaa tatcgtatat gtgccaaccg ctggtacgat actagtacca     720
atgccgaatg gaggaatag  agaaggtaaa ctaattgatg tctcagcaga aatgatggct     780
gagaattttg ccattgattt catggatgat gatgcaatac ttcagacaga aactggagtt     840
ggagtctatt cctttccaat gtgtaaccgc attagattca ggatctctcc atgggatatg     900
caaaaagatc aagatggtct aggcacagtt catatgacga actgggcaca ggggacggct     960
gccaggcaac cagctatctc tttcatgttc gaaactcgtg ataccttac tcaaggtgac     1020 taccaacatt tatccaagtg cacacccaag tcacaatatg tgttggacac agttttccct    1080
gaaacatcat tcgtaaacaa accaaacatc gactggaaca ttcagagcct acttacttcc    1140
actattcaac cagtatggtg taagaaaata gcaattttag tgtctgcata cgctgcgaaa    1200
atctgatccg gcgtcagcct ccaaaggagg tgcttcgaga ggtgtgaaaa aagaataca     1259
```

<210> SEQ ID NO 14
<211> LENGTH: 391
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: VP6
<220> FEATURE:
<221> NAME/KEY: MOD_RES
<222> LOCATION: (179)..(179)
<223> OTHER INFORMATION: Any amino acid

<400> SEQUENCE: 14

```
Met Asp Leu Ile Glu Thr Val Asn Ala Cys Val Arg Leu Gln Lys Arg
1               5                   10                  15

Ile Leu Asn Leu Ala Pro Asn Thr Asn Leu Asn Thr Ser Gly Gln Ser
            20                  25                  30

Thr Leu Asn Asp Tyr Asn Ala Leu Ala Ser Arg Cys Asn Gly Arg Thr
        35                  40                  45

Tyr Ala Phe Leu Asp Gln Thr Ala Val Leu Thr Pro Phe Thr Ile Asn
    50                  55                  60

Ala Pro Ile Ile Ser Leu Ser Val Arg Ile Ser Thr Asp Asp Tyr Asp
65                  70                  75                  80

Asp Met Arg Ser Gly Ile Asn Ser Ile Leu Asp Val Leu Ala Ala Ala
                85                  90                  95

Ile Arg Thr Glu Gly Ser Arg Pro Val Arg Ala Ile Glu Arg Arg Val
            100                 105                 110

Leu Glu Pro Ala Val Lys Gln Leu Val Glu Asp Leu Lys Leu Lys Ser
        115                 120                 125
```

| | | | | | | | | | | | |
|---|---|---|---|---|---|---|---|---|---|---|---|
Leu Thr Ser Glu Ile Ser Val Ala Asn Leu Ala Ala Val Asp Thr Ala
    130                      135                      140

Ile Ile Gln Pro Glu Ile Gln Thr Glu Asn Pro Leu Tyr Ala Asp
145                    150                      155                      160

Val Ile Glu Gln Val Val Asn Arg Pro Gln Met Asn Met Thr Gly Gly
    165                      170                      175

Asn Ile Xaa Ala Thr Leu Gly Arg Trp Ser Gly Asn Lys Gly Val Val
        180                      185                      190

Thr Cys Met Ser Gly Met Asp Ser Glu His Arg Phe Thr Val Asp Leu
    195                      200                      205

Lys Ala Arg Thr Thr Gly Ile Ile Asn Ile Val Tyr Val Pro Thr Ala
210                    215                      220

Gly Thr Ile Leu Val Pro Met Pro Asn Gly Arg Asn Arg Glu Gly Lys
225                    230                      235                      240

Leu Ile Asp Val Ser Ala Glu Met Met Ala Glu Asn Phe Ala Ile Asp
        245                      250                      255

Phe Met Asp Asp Asp Ala Ile Leu Gln Thr Glu Thr Gly Val Gly Val
        260                      265                      270

Tyr Ser Phe Pro Met Cys Asn Arg Ile Arg Phe Arg Ile Ser Pro Trp
    275                      280                      285

Asp Met Gln Lys Asp Gln Asp Gly Leu Gly Thr Val His Met Thr Asn
290                    295                      300

Trp Ala Gln Gly Thr Ala Ala Arg Gln Pro Ala Ile Ser Phe Met Phe
305                    310                      315                      320

Glu Thr Arg Asp Thr Phe Thr Gln Gly Asp Tyr Gln His Leu Ser Lys
        325                      330                      335

Cys Thr Pro Lys Ser Gln Tyr Val Leu Asp Thr Val Phe Pro Glu Thr
        340                      345                      350

Ser Phe Val Asn Lys Pro Asn Ile Asp Trp Asn Ile Gln Ser Leu Leu
    355                      360                      365

Thr Ser Thr Ile Gln Pro Val Trp Cys Lys Lys Ile Ala Ile Leu Val
370                    375                      380

Ser Ala Tyr Ala Ala Lys Ile
385                    390

```
<210> SEQ ID NO 15
<211> LENGTH: 972
<212> TYPE: DNA
<213> ORGANISM: Unknown
<220> FEATURE:
<223> OTHER INFORMATION: Description of Unknown:
      Reoviridae family sequence

<400> SEQUENCE: 15
tattgtgttt gattcacata gctcgctgag agtcaagcac aatggccttg aacgtgatcg      60
tgtctgttct gaagaacgta ttgaatgagt tgagtgttga aagtctgat gtgataactg     120 ataaattcaa ggaggcttta aacgactgtg gcattagagt cgatgattgg agagatgctt     180
tctacaacga gagaatacca aagccaatgt cttccacctc aatggcgatg caactgaaga     240
actttgaact tgaggtacta cagcttagaa acagagcttg gttagaggga gctgataggga     300 aaaacagatt gttttcgagt tttgatatct ccggcaaaaa tggacataca gttcttatac     360
cgaaaacaag aaatgctcag atgttgttgg ctaactctgt ggccgactta aaatcagaa     420 atggccagtc tgaagtcatt gatgatctaa ttaagaagaa tgaggagcta aagagacaat     480
```

```
tggaccaatt tacagtagct gtagagaatc aagagaact tcagataact tatcaggttg    540
aggcagctac cgcaaaaatg acggaactgt ctgatctgct taaggtgtgc caaaatgaat    600
gcgttaaact tcaaaaaaga ctgacgttcc aagaggaaca gactgatgat agaattgccg    660
caatcaatat gcatcatgct gaagaaacaa aaattcttaa aagggaaatt gaacgacwwa    720
acatagtaaa tgcatgtgtg aaggattaca acgatgtgtt ggaaaaacag catgaaagaa    780
atctaaaaat aattcgagga ctagctttaa aggctggttt actggttgaa gattcagacg    840
atgaagtaga agtggacagc atgaaacaag aaaaatgaat gattgatatg aacggaattt    900
aaacttcatg acatagacgc gtcgcacgtt taaggataaa aagttggact gaccacccaa    960
tcactaaaaa cc                                                       972
```

<210> SEQ ID NO 16
<211> LENGTH: 278
<212> TYPE: PRT
<213> ORGANISM: Unknown
<220> FEATURE:
<223> OTHER INFORMATION: Description of Unknown:
     Reoviridae family sequence
<220> FEATURE:
<223> OTHER INFORMATION: Nsp3
<220> FEATURE:
<221> NAME/KEY: MOD_RES
<222> LOCATION: (226)..(226)
<223> OTHER INFORMATION: Any amino acid

<400> SEQUENCE: 16

```
Met Ala Leu Asn Val Ile Val Ser Val Leu Lys Asn Val Leu Asn Glu
1               5                   10                  15

Leu Ser Val Glu Lys Ser Asp Val Ile Thr Asp Lys Phe Lys Glu Ala
            20                  25                  30

Leu Asn Asp Cys Gly Ile Arg Val Asp Asp Trp Arg Asp Ala Phe Tyr
        35                  40                  45

Asn Glu Arg Ile Pro Lys Pro Met Ser Ser Thr Ser Met Ala Met Gln
    50                  55                  60

Leu Lys Asn Phe Glu Leu Glu Val Leu Gln Leu Arg Asn Arg Ala Trp
65                  70                  75                  80

Leu Glu Gly Ala Asp Arg Lys Asn Arg Leu Phe Ser Ser Phe Asp Ile
                85                  90                  95

Ser Gly Lys Asn Gly His Thr Val Leu Ile Pro Lys Thr Arg Asn Ala
            100                 105                 110

Gln Met Leu Leu Ala Asn Ser Val Ala Asp Leu Lys Ile Arg Asn Gly
        115                 120                 125

Gln Ser Glu Val Ile Asp Asp Leu Ile Lys Lys Asn Glu Glu Leu Lys
    130                 135                 140

Arg Gln Leu Asp Gln Phe Thr Val Ala Val Glu Asn Pro Arg Glu Leu
145                 150                 155                 160

Gln Ile Thr Tyr Gln Val Glu Ala Ala Thr Ala Lys Met Thr Glu Leu
                165                 170                 175

Ser Asp Leu Leu Lys Val Cys Gln Asn Glu Cys Val Lys Leu Gln Lys
            180                 185                 190

Arg Leu Thr Phe Gln Glu Glu Gln Thr Asp Asp Arg Ile Ala Ala Ile
        195                 200                 205

Asn Met His His Ala Glu Glu Thr Lys Ile Leu Lys Arg Glu Ile Glu
    210                 215                 220

Arg Xaa Asn Ile Val Asn Ala Cys Val Lys Asp Tyr Asn Asp Val Leu
225                 230                 235                 240
```

Glu Lys Gln His Glu Arg Asn Leu Lys Ile Ile Arg Gly Leu Ala Leu
                245                 250                 255

Lys Ala Gly Leu Leu Val Glu Asp Ser Asp Asp Glu Val Glu Val Asp
            260                 265                 270

Ser Met Lys Gln Glu Lys
        275

<210> SEQ ID NO 17
<211> LENGTH: 1030
<212> TYPE: DNA
<213> ORGANISM: Unknown
<220> FEATURE:
<223> OTHER INFORMATION: Description of Unknown:
      Reoviridae family sequence

<400> SEQUENCE: 17
ggttttaaaa tagttggtgt agtgtgtcgt gagagggctc catcaccctg gtcaccatga    60
cgcagtctat ttctcttgct gactttgtta caaaaactga tgacggtttc atgccatctg   120
atcgtgagtg cactgttttg gatcgatact tgtcaaaaga tcagaaagaa ttacgcgaaa   180
cgtacaagga tgaaaagaat catagagcat cactcagagt caagatgttt ctaacttctg   240
caccatcacg caggttcaca cagcaaggtg tcgtgccaat gcgtgaatta agaacgaact   300
cagacatacc gagctcactt ttaaatatta tcactgattg gttgatgaac gttctgagcg   360
atgaggaaaa tcaggagatg tttgaagaat ttattagctc aaaatttcca gatattcttg   420
gatcagctga taagctggct agatttgctt tgagactgga gaacaaaaga gacataaatac   480 acaaaaactt ttcgaaagcc atgaatgctt ttggaacatg ttttctcgcc gtcaaaccaa   540
cttatgcaac agaaggtcag tgtaatgttg tacgtgccac ggacgatgca atcatttttag   600 agtttcaacc aattccagaa tattatagat gtggcaggtc aagatctacc ttctataagt   660
tatacccgct ttcagaagag caaccagtta caggaatgat tgcattaagg ggaattgcag   720
ggaatcaact tataatgaat catggacatg ggcatctaag aaccgtacca taccatgaaa   780
tagctgatgc aatcaaatca tttgcaaaga aggacaaaga acattagaa ctgatctcca   840 aatcacctct ttcagcacag tgcggaagca aatttttgga catgcttgac ggtatcagat   900
cgaagcagag aattgaggat gtgattgcca aagcgaagac ttttgaaaag aaaaaaccat   960
gaatatggag tcaaaagata aatatgacyg tgataaatcc gctacatcgg ctattaacat  1020
ataaaaaccc                                                          1030

<210> SEQ ID NO 18
<211> LENGTH: 301
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: Nsp2

<400> SEQUENCE: 18

Met Thr Gln Ser Ile Ser Leu Ala Asp Phe Val Thr Lys Thr Asp Asp
1               5                   10                  15

Gly Phe Met Pro Ser Asp Arg Glu Cys Thr Val Leu Asp Arg Tyr Leu
            20                  25                  30

Ser Lys Asp Gln Lys Glu Leu Arg Glu Thr Tyr Lys Asp Glu Lys Asn
        35                  40                  45

His Arg Ala Ser Leu Arg Val Lys Met Phe Leu Thr Ser Ala Pro Ser
 50                  55                  60

Arg Arg Phe Thr Gln Gln Gly Val Val Pro Met Arg Glu Leu Arg Thr
 65                  70                  75                  80

Asn Ser Asp Ile Pro Ser Ser Leu Leu Asn Ile Ile Thr Asp Trp Leu
                 85                  90                  95

Met Asn Val Leu Ser Asp Glu Glu Asn Gln Glu Met Phe Glu Glu Phe
            100                 105                 110

Ile Ser Ser Lys Phe Pro Asp Ile Leu Gly Ser Ala Asp Lys Leu Ala
            115                 120                 125

Arg Phe Ala Leu Arg Leu Glu Asn Lys Arg Asp Ile Ile His Lys Asn
130                 135                 140

Phe Ser Lys Ala Met Asn Ala Phe Gly Thr Cys Phe Leu Ala Val Lys
145                 150                 155                 160

Pro Thr Tyr Ala Thr Glu Gly Gln Cys Asn Val Val Arg Ala Thr Asp
                165                 170                 175

Asp Ala Ile Ile Leu Glu Phe Gln Pro Ile Pro Glu Tyr Tyr Arg Cys
            180                 185                 190

Gly Arg Ser Arg Ser Thr Phe Tyr Lys Leu Tyr Pro Leu Ser Glu Glu
            195                 200                 205

Gln Pro Val Thr Gly Met Ile Ala Leu Arg Gly Ile Ala Gly Asn Gln
210                 215                 220

Leu Ile Met Asn His Gly His Gly His Leu Arg Thr Val Pro Tyr His
225                 230                 235                 240

Glu Ile Ala Asp Ala Ile Lys Ser Phe Ala Lys Lys Asp Lys Glu Thr
                245                 250                 255

Leu Glu Leu Ile Ser Lys Ser Pro Leu Ser Ala Gln Cys Gly Ser Lys
            260                 265                 270

Phe Leu Asp Met Leu Asp Gly Ile Arg Ser Lys Gln Arg Ile Glu Asp
            275                 280                 285

Val Ile Ala Lys Ala Lys Thr Phe Glu Lys Lys Lys Pro
290                 295                 300

<210> SEQ ID NO 19
<211> LENGTH: 745
<212> TYPE: DNA
<213> ORGANISM: Unknown
<220> FEATURE:
<223> OTHER INFORMATION: Description of Unknown:
      Reoviridae family sequence

<400> SEQUENCE: 19
ggtattatag agtcttagga tggctgagga cggcgaaatg gaacaaatga taatagatac    60
tctgtataat caaattctta atttagctgg aaatacgacg catgaaaaca tcaaacaaac   120
tatttcaaac tcttcgccgc aaaagatttt aactggcgca ttttttaacat taggaacatt   180
gttaacaaca attgtattta agagaaaggg aatcaatcta cttacgagta aatttaagtc   240
caacattacg tatttagctg aaatattggt atggaaggct gagcagacag taaatgagat   300
aattgagaag acattacagc aacacaagtt tatgagggaa aaagatattg atggtgtttt   360
gaaggacatt aagaaaatga aatatgacat agaacatatt ggtggattag acgtaacgaa   420
agaacttttt tcaatgtgtg aacgcaaaat gatcgattta gatgataaaa tgagagacat   480
agaaaaatct tgtgatagaa gaatacggga ttacgactgg aaaataaacg cactaacact   540
acatccgata cagcaagctg cggtgcagag cgaaacagca gaaagaacg acaaaattga   600

```
aatcgtagat gaaacagtac aaaacacacg cagtaagcct attaaaactc gtctggctcc    660
caaaagactc taacgacttg tggaataatt aggagaagat ctctctgtgg ttattcctcc    720
ccatcaagtc aagcgacata aaacc                                          745
```

<210> SEQ ID NO 20
<211> LENGTH: 217
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: Nsp4

<400> SEQUENCE: 20

```
Met Ala Glu Asp Gly Glu Met Glu Gln Met Ile Ile Asp Thr Leu Tyr
1               5                   10                  15

Asn Gln Ile Leu Asn Leu Ala Gly Asn Thr Thr His Glu Asn Ile Lys
            20                  25                  30

Gln Thr Ile Ser Asn Ser Ser Pro Gln Lys Ile Leu Thr Gly Ala Phe
        35                  40                  45

Leu Thr Leu Gly Thr Leu Leu Thr Thr Ile Val Phe Lys Arg Lys Gly
    50                  55                  60

Ile Asn Leu Leu Thr Ser Lys Phe Lys Ser Asn Ile Thr Tyr Leu Ala
65                  70                  75                  80

Glu Ile Leu Val Trp Lys Ala Glu Gln Thr Val Asn Glu Ile Ile Glu
                85                  90                  95

Lys Thr Leu Gln Gln His Lys Phe Met Arg Glu Lys Asp Ile Asp Gly
            100                 105                 110

Val Leu Lys Asp Ile Lys Lys Met Lys Tyr Asp Ile Glu His Ile Gly
        115                 120                 125

Gly Leu Asp Val Thr Lys Glu Leu Phe Ser Met Cys Glu Arg Lys Met
    130                 135                 140

Ile Asp Leu Asp Asp Lys Met Arg Asp Ile Glu Lys Ser Cys Asp Arg
145                 150                 155                 160

Arg Ile Arg Asp Tyr Asp Trp Lys Ile Asn Ala Leu Thr Leu His Pro
                165                 170                 175

Ile Gln Gln Ala Ala Val Gln Ser Glu Thr Ala Glu Lys Asn Asp Lys
            180                 185                 190

Ile Glu Ile Val Asp Glu Thr Val Gln Asn Thr Arg Ser Lys Pro Ile
        195                 200                 205

Lys Thr Arg Leu Ala Pro Lys Arg Leu
    210                 215
```

<210> SEQ ID NO 21
<211> LENGTH: 583
<212> TYPE: DNA
<213> ORGANISM: Unknown
<220> FEATURE:
<223> OTHER INFORMATION: Description of Unknown:
      Reoviridae family sequence

<400> SEQUENCE: 21

```
ggtatataaa agtcagtaaa cggctggaaa cgttgaactg actactcatt gcccaggaat     60
ggctgaagca tctgagttca atttcaatac aagaaggaaa agaagaacaa ttactgagaa    120
acgtgagact aaagaggttg ttaaacagaa gatgcttgtt gacgagaaaa atgataatta    180
cgaagaagtt gagtcagctt cagtatattc tgcggaatca tccagaagca actatagtga    240
```

```
tgcatatgag aaacttaaac gtgaaccagt ggttgaagat tcaaatgatg aaaaatataa      300
aactttagaa tactcagaag acgaagaagt tttcaaatct gcattgaaac aaagtgacaa      360
accagctcga agcatcagca aaacacagca tgatgacagt actgattcta gtgttctcat      420
ggaaaaaata tccgaacttt ctttggaaat tgaaaagatg aaacagtcta atcaaccatt      480
yacagttgat gcagcattca atactacact cagaaatgtt gacaacctta ctacaagaca      540
gaaacaggcg ctgattatgg cactcgtaaa ttcaatgaac taa                        583
```

```
<210> SEQ ID NO 22
<211> LENGTH: 174
<212> TYPE: PRT
<213> ORGANISM: Unknown
<220> FEATURE:
<223> OTHER INFORMATION: Description of Unknown:
      Reoviridae family sequence
<220> FEATURE:
<223> OTHER INFORMATION: Nsp5
<220> FEATURE:
<221> NAME/KEY: MOD_RES
<222> LOCATION: (141)..(141)
<223> OTHER INFORMATION: Any amino acid

<400> SEQUENCE: 22
```

Met Ala Glu Ala Ser Glu Phe Asn Phe Asn Thr Arg Arg Lys Arg Arg
1               5                   10                  15

Thr Ile Thr Glu Lys Arg Glu Thr Lys Glu Val Val Lys Gln Lys Met
            20                  25                  30

Leu Val Asp Glu Lys Asn Asp Asn Tyr Glu Glu Val Glu Ser Ala Ser
        35                  40                  45

Val Tyr Ser Ala Glu Ser Ser Arg Ser Asn Tyr Ser Asp Ala Tyr Glu
    50                  55                  60

Lys Leu Lys Arg Glu Pro Val Val Glu Asp Ser Asn Asp Glu Lys Tyr
65                  70                  75                  80

Lys Thr Leu Glu Tyr Ser Glu Asp Glu Val Phe Lys Ser Ala Leu
            85                  90                  95

Lys Gln Ser Asp Lys Pro Ala Arg Ser Ile Ser Lys Thr Gln His Asp
            100                 105                 110

Asp Ser Thr Asp Ser Ser Val Leu Met Glu Lys Ile Ser Glu Leu Ser
            115                 120                 125

Leu Glu Ile Glu Lys Met Lys Gln Ser Asn Gln Pro Xaa Thr Val Asp
    130                 135                 140

Ala Ala Phe Asn Thr Thr Leu Arg Asn Val Asp Asn Leu Thr Thr Arg
145                 150                 155                 160

Gln Lys Gln Ala Leu Ile Met Ala Leu Val Asn Ser Met Asn
            165                 170

```
<210> SEQ ID NO 23
<211> LENGTH: 25
<212> TYPE: DNA
<213> ORGANISM: Artificial Sequence
<220> FEATURE:
<223> OTHER INFORMATION: RotaB Forward Primer

<400> SEQUENCE: 23
cagacgatct gatagggatg tattg                                            25

<210> SEQ ID NO 24
<211> LENGTH: 22
<212> TYPE: DNA
```

```
<213> ORGANISM: Artificial Sequence
<220> FEATURE:
<223> OTHER INFORMATION: RotaB Reverse Primer

<400> SEQUENCE: 24
atgtccgtga cgtagtatct tc                                              22

<210> SEQ ID NO 25
<211> LENGTH: 23
<212> TYPE: DNA
<213> ORGANISM: Artificial Sequence
<220> FEATURE:
<223> OTHER INFORMATION: Astrovirus Forward Primer

<400> SEQUENCE: 25
gtgcagatgt gttggcgtat aag                                             23

<210> SEQ ID NO 26
<211> LENGTH: 23
<212> TYPE: DNA
<213> ORGANISM: Artificial Sequence
<220> FEATURE:
<223> OTHER INFORMATION: Astrovirus Reverse Primer

<400> SEQUENCE: 26
tgaagcgtac aaaccaggat gag                                             23
```